US007826071B2

(12) United States Patent
Shchegrov et al.

(10) Patent No.: US 7,826,071 B2
(45) Date of Patent: Nov. 2, 2010

(54) PARAMETRIC PROFILING USING OPTICAL SPECTROSCOPIC SYSTEMS

(75) Inventors: Andrei V. Shchegrov, Campbell, CA (US); Anatoly Fabrikant, Fremont, CA (US); Mehrdad Nikoonahad, Menlo Park, CA (US); Ady Levy, Sunnyvale, CA (US); Daniel C. Wack, Los Altos, CA (US); Noah Bareket, Saratoga, CA (US); Walter Mieher, Los Gatos, CA (US); Ted Dziura, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 310 days.

(21) Appl. No.: 11/868,740

(22) Filed: Oct. 8, 2007
(Under 37 CFR 1.47)

(65) Prior Publication Data
US 2009/0135416 A1    May 28, 2009

Related U.S. Application Data

(63) Continuation of application No. 10/327,466, filed on Dec. 19, 2002, now Pat. No. 7,280,230.

(60) Provisional application No. 60/343,077, filed on Dec. 19, 2001.

(51) Int. Cl.
G01B 11/14    (2006.01)
(52) U.S. Cl. .................................... 356/625
(58) Field of Classification Search ............. None
See application file for complete search history.

(56) References Cited

U.S. PATENT DOCUMENTS 4,039,370 A    8/1977    Kleinknecht
(Continued)

FOREIGN PATENT DOCUMENTS

EP    0480620 A2    4/1992
(Continued)

OTHER PUBLICATIONS

International Search Report corresponding to PCT International Application No. PCT/US02/41151, filed Dec. 19, 2002, 7 pages.
(Continued)

*Primary Examiner*—Gregory J Toatley, Jr.
*Assistant Examiner*—Juan D Valentin
(74) *Attorney, Agent, or Firm*—Davis Wright Tremaine LLP

(57) ABSTRACT

A gallery of seed profiles is constructed and the initial parameter values associated with the profiles are selected using manufacturing process knowledge of semiconductor devices. Manufacturing process knowledge may also be used to select the best seed profile and the best set of initial parameter values as the starting point of an optimization process whereby data associated with parameter values of the profile predicted by a model is compared to measured data in order to arrive at values of the parameters. Film layers over or under the periodic structure may also be taken into account. Different radiation parameters such as the reflectivities $R_s$, $R_p$ and ellipsometric parameters may be used in measuring the diffracting structures and the associated films. Some of the radiation parameters may be more sensitive to a change in the parameter value of the profile or of the films then other radiation parameters. One or more radiation parameters that are more sensitive to such changes may be selected in the above-described optimization process to arrive at a more accurate measurement. The above-described techniques may be supplied to a track/stepper and etcher to control the lithographic and etching processes in order to compensate for any errors in the profile parameters.

24 Claims, 13 Drawing Sheets

U.S. PATENT DOCUMENTS

| | | | |
|---|---|---|---|
| 4,141,780 A | 2/1979 | Kleinknecht et al. |
| 4,200,396 A | 4/1980 | Kleinknecht et al. |
| 4,303,341 A | 12/1981 | Kleinknecht et al. |
| 4,330,213 A | 5/1982 | Kleinknecht et al. |
| 4,408,884 A | 10/1983 | Kleinknecht et al. |
| 4,668,860 A | 5/1987 | Anthon |
| 4,672,196 A | 6/1987 | Canino |
| 4,695,162 A | 9/1987 | Itonaga et al. |
| 4,710,642 A | 12/1987 | McNeil |
| 4,790,659 A | 12/1988 | Erman et al. |
| 4,905,170 A | 2/1990 | Forouhi et al. |
| 4,991,971 A | 2/1991 | Geary et al. |
| 4,999,014 A | 3/1991 | Gold et al. |
| 5,032,734 A | 7/1991 | Orazio, Jr. et al. |
| 5,042,951 A | 8/1991 | Gold et al. |
| 5,076,696 A | 12/1991 | Cohn et al. |
| 5,164,790 A | 11/1992 | McNeil et al. |
| 5,166,752 A | 11/1992 | Spanier et al. |
| 5,241,369 A | 8/1993 | McNeil et al. |
| 5,329,357 A | 7/1994 | Bernoux et al. |
| 5,333,052 A | 7/1994 | Finarov |
| 5,337,146 A | 8/1994 | Azzam |
| 5,365,340 A | 11/1994 | Ledger |
| 5,381,233 A | 1/1995 | Chao et al. |
| 5,408,322 A | 4/1995 | Hsu |
| 5,412,473 A | 5/1995 | Rosenewaig et al. |
| 5,416,594 A | 5/1995 | Gross et al. |
| 5,420,680 A | 5/1995 | Isobe et al. |
| 5,432,607 A | 7/1995 | Taubenblatt |
| 5,494,697 A | 2/1996 | Blayo et al. |
| 5,503,707 A | 4/1996 | Maung et al. |
| 5,504,582 A | 4/1996 | Johs et al. |
| 5,521,706 A | 5/1996 | Green et al. |
| 5,526,117 A | 6/1996 | Wielsch et al. |
| 5,596,411 A | 1/1997 | Fanton et al. |
| 5,604,581 A | 2/1997 | Liu et al. |
| 5,607,800 A | 3/1997 | Ziger |
| 5,608,526 A | 3/1997 | Piwonka-Corle et al. |
| 5,610,392 A | 3/1997 | Nagayama et al. |
| 5,625,455 A | 4/1997 | Nash et al. |
| 5,631,171 A | 5/1997 | Sandstrom et al. |
| 5,638,178 A | 6/1997 | Lacey et al. |
| 5,638,199 A | 6/1997 | Tsubota et al. |
| 5,666,201 A | 9/1997 | Johs et al. |
| 5,739,909 A | 4/1998 | Blayo et al. |
| 5,747,813 A | 5/1998 | Norton et al. |
| 5,751,427 A | 5/1998 | De Groot |
| 5,757,671 A | 5/1998 | Drevillon et al. |
| 5,805,290 A | 9/1998 | Ausschnitt et al. |
| 5,825,498 A | 10/1998 | Thakur et al. |
| 5,835,221 A | 11/1998 | Lee et al. |
| 5,867,276 A | 2/1999 | McNeil et al. |
| 5,880,838 A | 3/1999 | Marx |
| 5,900,939 A | 5/1999 | Aspnes et al. |
| 5,923,423 A | 7/1999 | Sawatari et al. |
| 5,956,148 A | 9/1999 | Celii |
| 5,963,329 A | 10/1999 | Conrad et al. |
| 5,978,074 A | 11/1999 | Opsal et al. |
| 6,031,615 A | 2/2000 | Meeks et al. |
| 6,097,488 A | 8/2000 | Grek et al. |
| 6,100,985 A | 8/2000 | Scheiner et al. |
| 6,104,486 A | 8/2000 | Arimoto |
| 6,118,525 A | 9/2000 | Fossey et al. |
| 6,268,916 B1 | 7/2001 | Lee et al. |
| 6,271,047 B1 | 8/2001 | Ushio et al. |
| 6,278,519 B1 | 8/2001 | Rosenewaig et al. |
| 6,323,946 B1 | 11/2001 | Norton |
| 6,483,580 B1 | 11/2002 | Xu et al. |
| 6,590,656 B2 | 7/2003 | Xu et al. |
| 6,603,542 B1 | 8/2003 | Chase et al. |
| 6,614,540 B1 | 9/2003 | Stirton |
| 6,657,736 B1 | 12/2003 | Finarov et al. |
| 6,678,043 B1 | 1/2004 | Vurens et al. |
| 6,728,663 B2 | 4/2004 | Krukar et al. |
| 6,768,967 B2 | 7/2004 | Johnson et al. |
| 6,819,426 B2 * | 11/2004 | Sezginer et al. ............. 356/401 |
| 6,829,057 B2 | 12/2004 | Opsal et al. |
| 6,900,892 B2 | 5/2005 | Shchegrov et al. |
| 7,003,149 B2 | 2/2006 | Benesch et al. |
| 7,099,005 B1 | 8/2006 | Fabrikant et al. |
| 7,173,699 B2 | 2/2007 | Xu et al. |
| 7,515,253 B2 | 4/2009 | Bareket et al. |
| 2004/0107066 A1 | 6/2004 | Poolla et al. |

FOREIGN PATENT DOCUMENTS

| | | |
|---|---|---|
| EP | 0480620 A3 | 4/1992 |
| EP | 1124163 A2 | 8/2001 |
| EP | 1073876 B1 | 12/2004 |
| EP | 1508772 A1 | 2/2005 |
| EP | 1124163 A3 | 7/2005 |
| WO | PCT/US99/04053 | 2/1999 |
| WO | WO 99/45340 | 9/1999 |
| WO | WO 00/35002 | 6/2000 |
| WO | WO 02/50501 A1 | 6/2002 |

OTHER PUBLICATIONS

"Ultraviolet-visible ellipsometry for process control during the etching of submicrometer features," N. Blayo et al., *J. Opt. Soc. Am. A*, vol. 12, No. 3, Mar. 1995, pp. 591-599.

International Preliminary Examination Report for PCT/US99/04053 mailed Jul. 3, 2000.

Written Opinion for PCT/US99/04053, mailed Mar. 27, 2000.

"Optical dispersion relations for amorphous semiconductors and amorphous dielectrics," A.R. Forouhi et al., *Physical Review B*, vol. 34, No. 10, Nov. 15, 1986, pp. 7018-7026.

"Optical properties of crystalline semiconductors and dielectrics," A.R. Forouhi et al., *Physical Review B*, vol. 38, No. 3, Jul. 15, 1988, pp. 1865-1873.

"Optical characterization of amorphous and polycrystalline silicon films," E. Ibok et al., *Solid State Technology*, Aug. 1995.

"Convergence of the coupled-wave method for metallic lamellar diffraction gratings," L. Li et al., *Journal of the Optical Society of America A*, vol. 10, No. 6, Jun. 1993, pp. 1184-1188.

"Multilayer modal method for diffraction gratings of arbitrary profile, depth, and permitivity," L. Li, *Journal of the Optical Society of America A*, vol. 10, No. 12, Dec. 1993, pp. 2581-2591.

"A model analysis of lamelar diffraction gratings in a conical mounting," L. Li, *Journal of Modern Optics*, vol. 40, No. 4, 1993, pp. 553-573.

"Metrology of subwavelength photoresist gratings using optical scatterometry," C.J. Raymond et al., *J. Vac. Sci. Technol. B*, vol. 13, No. 4, Jul./Aug. 1995, pp. 1484-1495.

"Line size effects on ultraviolet reflectance spectra," D.H. Ziger et al., *Opt. Eng.*, vol. 36, No. 1, Jan. 1997, pp. 243-250.

"Scatterometry and the Simulation of Diffraction-Based Metrology," S. Sohail et al., *Microlithography World*, Jul./Aug./Sep. 1993, pp. 5-16.

"A broadband UV small spot spectroscopic ellipsometer," T.R. Corle, *SPIE Microlithography*, 1995, pp. 1-12.

"Rigorous coupled-wave analysis of planar-grating diffraction," M.G. Moharam et al., *J. Opt. Soc. Am.*, vol. 71, No. 7, Jul. 1981, pp. 881-818.

"Stable implementation of the rigorous coupled-wave analysis for surface-relief gratings: enhanced transmittance matrix approach," M.G. Moharam et al., *J. Opt. Soc. Am. A*, vol. 12, No. 5, May 1995, pp. 1077-1086.

Pforr, R. et al., "In-Process Image Detecting Technique For Determination of Overlay and Image Quality for ASM-L Wafer Stepper" *SPIE*, vol. 1674 *Optical Laser Microlithography V* (1992).

Mills. D. W. et al., "Spectral ellipsometry on patterned wafers", *SPIE's Microelectronic Manufacturing: Process, Equipment, and Materials Control in Integrated Circuit Manufacturing, Spie* vol. 2637, Austin (USA), 1995.

Gaylord, T.K. et al., Analysis and Applications of Optical Diffraction by Gratings, *Proceedings of the IEEE*, vol. 73, No. 5, May 1985, pp. 894-937.

M. G. Moharam, "Coupled-wave analysis of Two-Dimensional Dielectric Gratings," *PROC. SPIE*, vol. 883, pp. 8-11 (1988).

M. G. Moharam, E. B. Grann, D. A. Pommet, and T. K. Gaylord, "Formulation of stable and efficient implementation of the rigorous coupled-wave analysis of binary gratings," *J. Opt. Soc. Am. A*, vol. 12, pp. 1068-1076 (1995).

L. Li, "Formulation and comparison of two recursive matrix algorithms for modeling layered diffraction gratings," *J. Opt. Soc. Am. A*, vol. 13, pp. 1024-1035 (1996).

McNeil, J. R., et al. "Scatterometry applied to microelectronics processing", Part 1, *Solid State Technology*, Mar. 1993.

McNeil, J. R., et al. "Scatterometry applied to microelectronics processing", Part 2, *Solid State Technology*, Apr. 1993.

PCT/US99/04053, filed Feb. 25, 1999.

Arimoto, H., "Precise Line-and-Space Monitoring Results by Ellipsometry", *Jpn. J. Appl. Phys.* vol. 36, Part 2, No. 2A, Feb. 1997, pp. L173-L175.

Azzam, "Ellipsometry," Handbook of Optics, vol. 2, Devices, Measurements and Properties, Second Edition, Optical Society of America, McGraw Hill, Inc., 1995, 27 pages.

Aspnes, "Effects of component optical activity in data reduction and calibration of rotating-analyzer ellipsometers," Journal of Optical Society of America, vol. 64, No. 6, Jun. 1974, 7 pages.

Bernoux et al., "Ellipsometire," Techniques de l'Ingenier, 1990, R6490, pp. 1-16 (28 pages of translation included).

Chipman, "Polarimetry," Handbook of Optics, vol. 2, Devices, Measurements and Properties, Second Edition, Optical Society of America, McGraw Hill, Inc., 1995, 37 pages.

Collins, "Automatic rotating element ellipsometers: Calibration, operation, and real-time applications," Rev. Sci Instrum. 61, (8), Aug. 1990, 33 pages.

Haggans et al., "Effective-Medium Theory of Zeroth-Order Lamellar Gratings in Conical Mountings," J. Opt. Soc. Am. A, Oct. 19, 1993, vol. 10, No. 10, pp. 2217-2225.

Kikuta et al., "Effective Medium Theory of Two-Dimensional Subwavelength Gratings in the Non-Quazi-Static limit," J. Opt. Soc. Am. A, vol. 15, No. 6, Jun. 1998, pp. 1577-1585.

Lalanne et al., "High-Order Effective-Medium Theory of Subwavelength Gratings in Classical Mounting: Application to Volume Holograms," J. Opt. Soc. Am. A, vol. 15, No. 7, Jul. 1998, pp. 1843-1851.

Lalanne e tal., "On the Effective Medium Theory of Subwavelength Periodic Structures," Jouranl of Modern Optics, 1996, vol. 43, No. 10, pp. 2063-2085.

Schramm et al., "Algorithm Implementation and Techniques for Providing More Reliable Overlay Measurements and Better Tracking of the Shallow Trench Isolation (STI) Process," SPIE: Conference on Methrology, Inspection, and Process Control of Microlithography XIII, Mar. 1999, pp. 116-122.

Tompkins et al., "Spectroscopic Ellipsometry and Reflectometry: A User's Guide," John Wiley & Sons, Inc., New York, 1999, 9 pages.

Wang et al., "Influence of semiconducor manufacturing process variation on device parameter measurement for angular scatterometry," SPIE Microlithography World 2006, 9 pages.

Yasuda and Aspens, "Optical-standard surfaces of single-crystal silicon for calibrating ellipsometers and reflectometers," Applied Optics, vol. 33, No. 31, Nov. 1994, Optical Society of America.

JPO, Decision of Refusal mailed in related Japanese Patent Application No. 2003-555142 on Jun. 4, 2009, 2 pages, and pending claims.

"Developed Photoresist Metrology Using Scatterometry" Murnane et al., (1994) Center for High Technology Materials, University of New Mexico, SPIE vol. 2196, pp. 47-59.

"Ellipsometric-Scatterometry for sub-0.1 μm CD measurements", Coulombe et al., (1998) Center for High Technology Materials, University of New Mexico, SPIE vol. 3332, pp. 282-292.

Diffraction: www.scienceworld.wolfram.com/physics/Diffraction.html (2004).

European Patent Office, "Communication of the European Search Report", mailed in EP 04078145.2 on Dec. 28, 2004.

"Polarization aberrations of crossed folding mirrors," Crandall and Chipman, (1995) SPIE, vol. 2537, 10 pages.

* cited by examiner

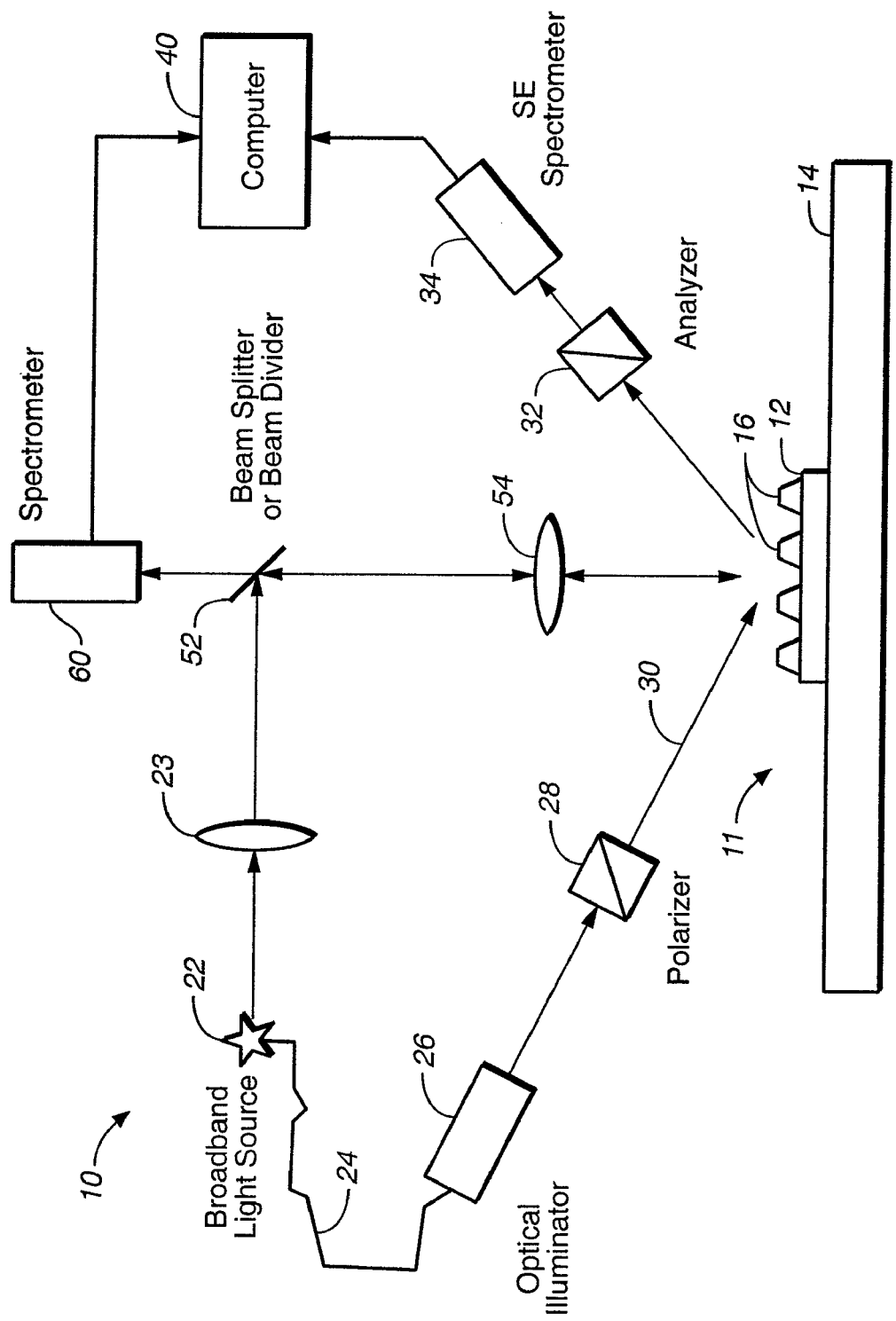
FIG._1A

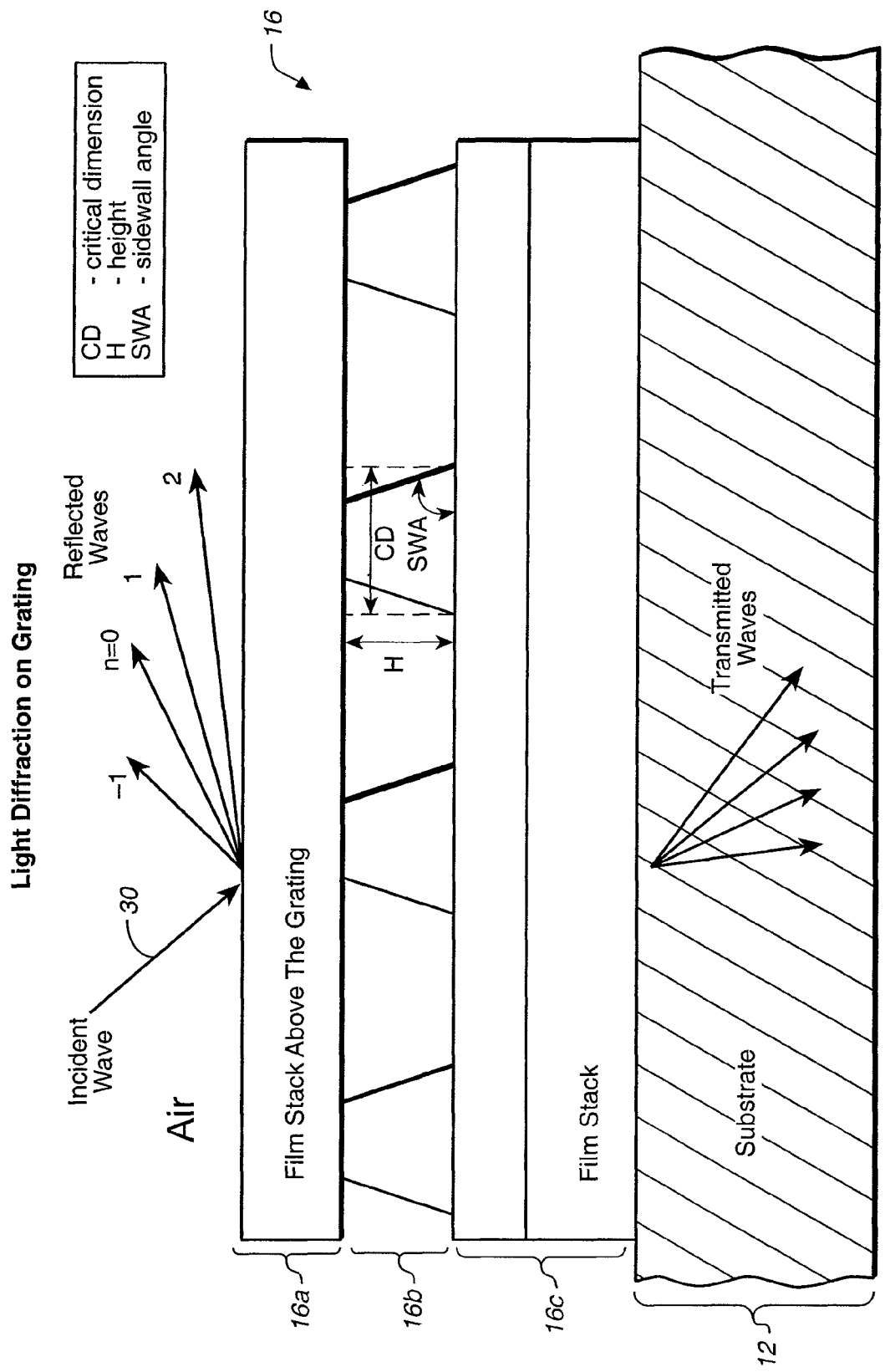
FIG._1B

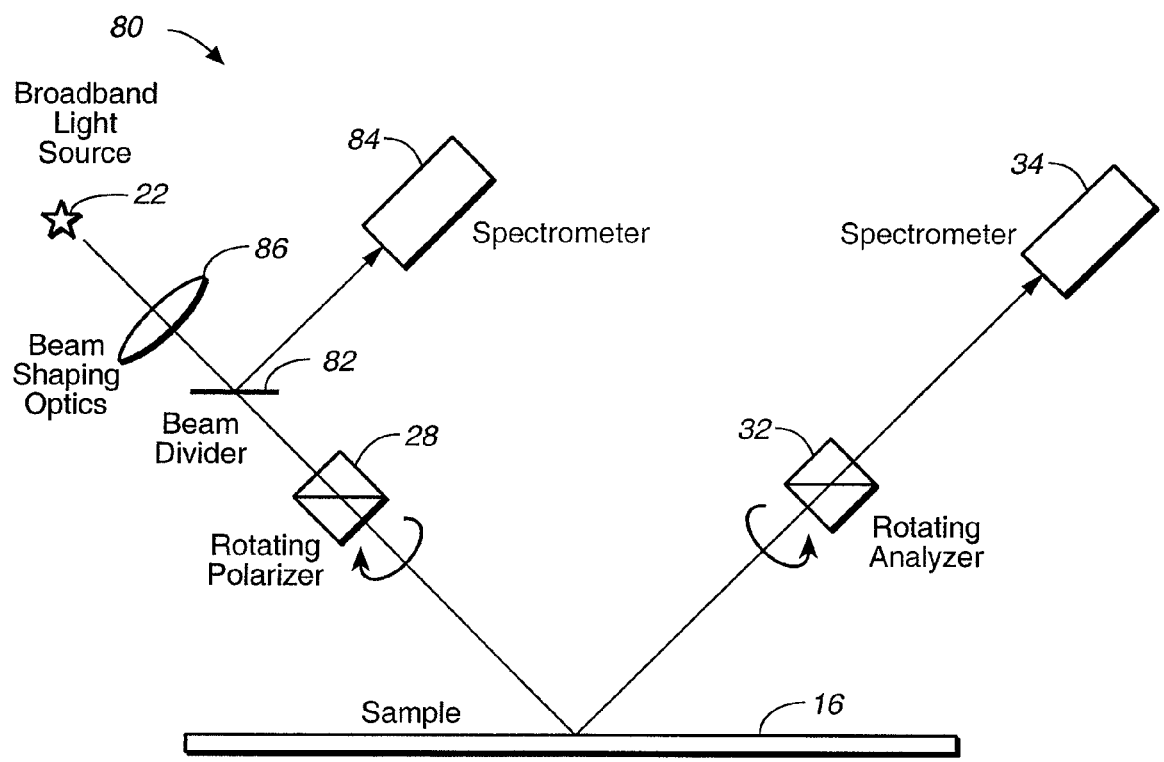
FIG._2

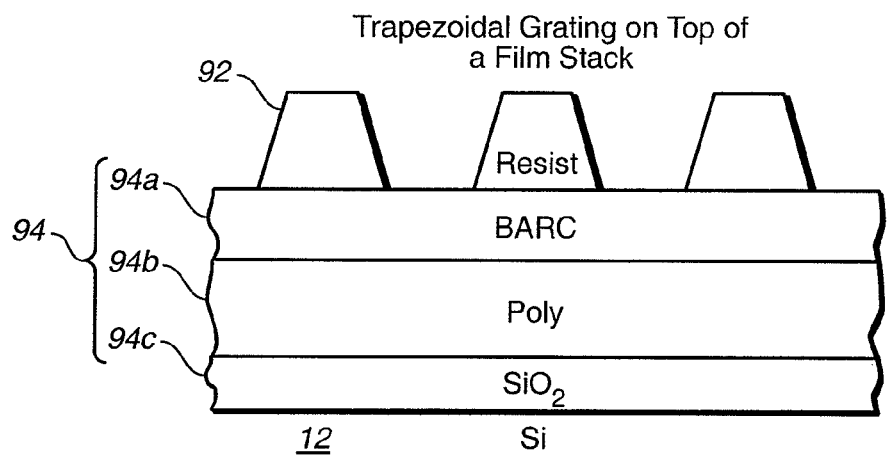
FIG._3A
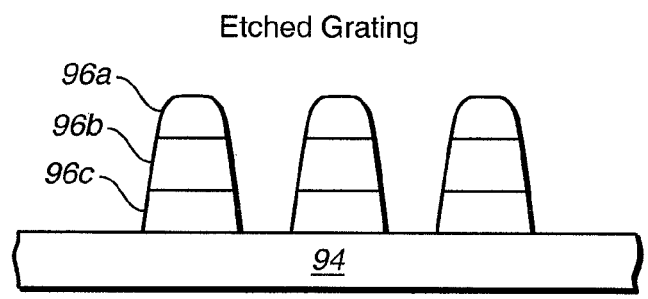
FIG._3B
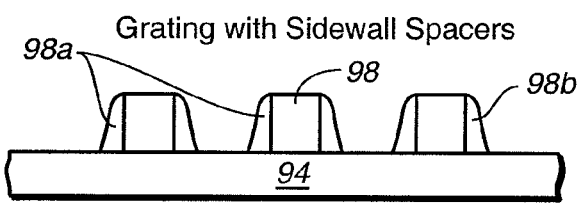
FIG._3C
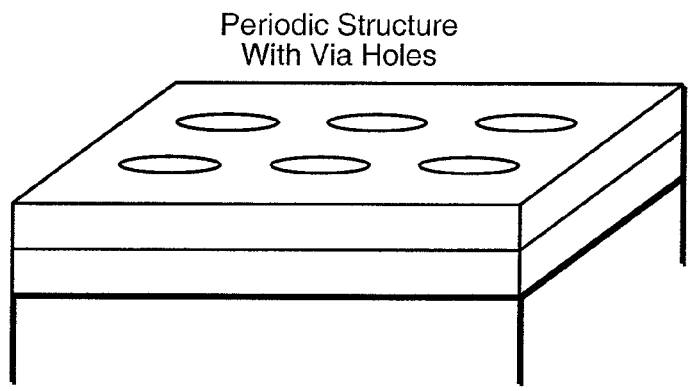
FIG._3D

Single-material,
Multi-Trapezoid Profile
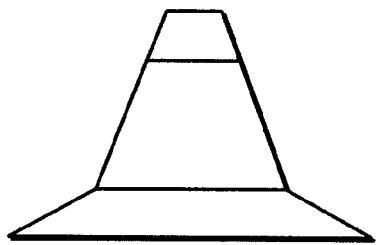
FIG._4A
Single-material,
Quartic Profile
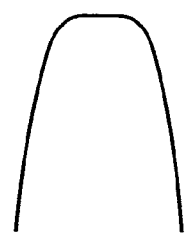
FIG._4B
Single-material Quartic Profile
with a Bottom Rounding
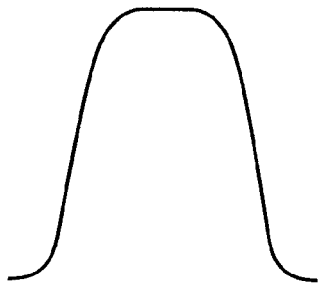
FIG._4C
Multi-material Etched Profile
Base on the Quartic Model
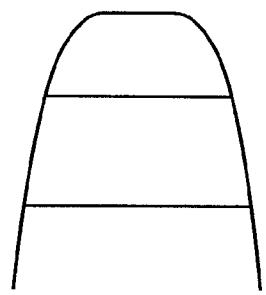
FIG._4D
Two-material Profile
with Sidewall Spacers
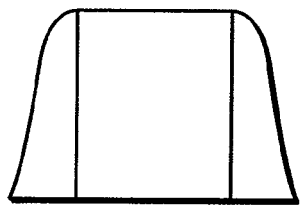
FIG._4E
3-dimensional Via Hole Profile
— a Hole in a Uniform Layer
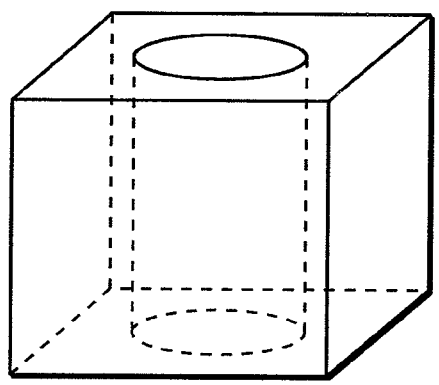
FIG._4F

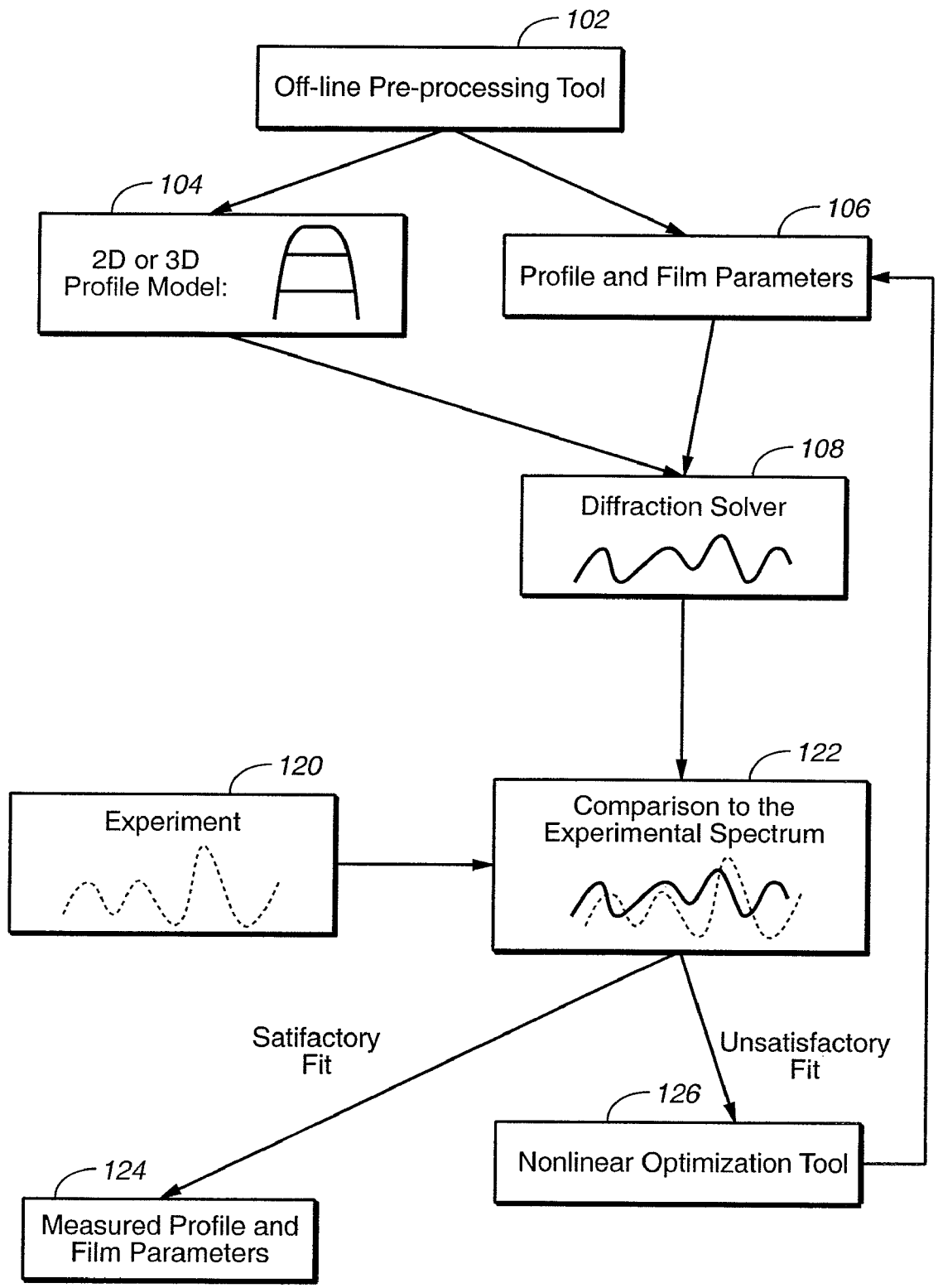
FIG._5A

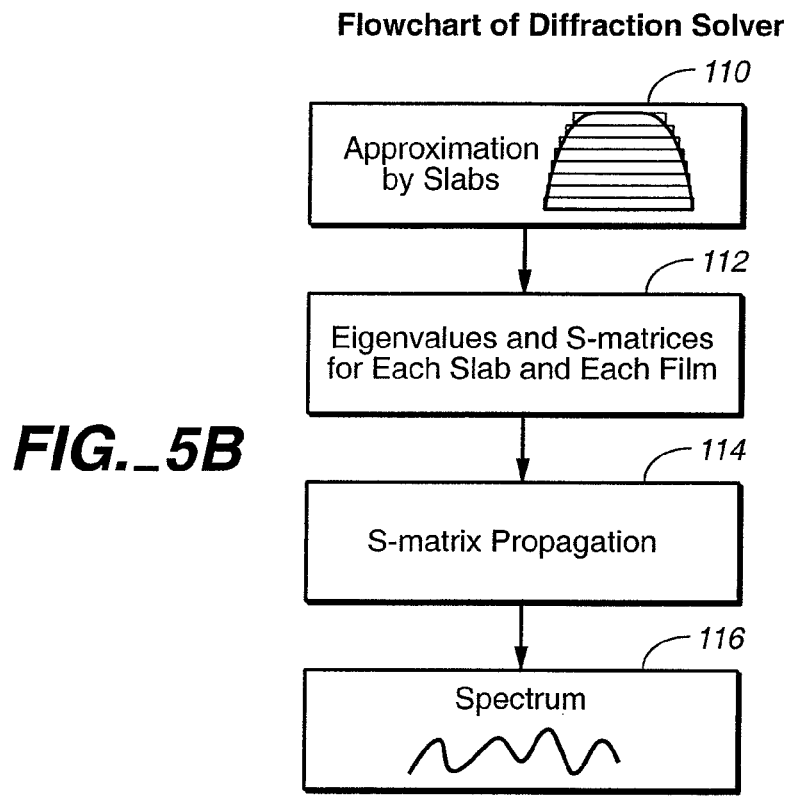
FIG._5B
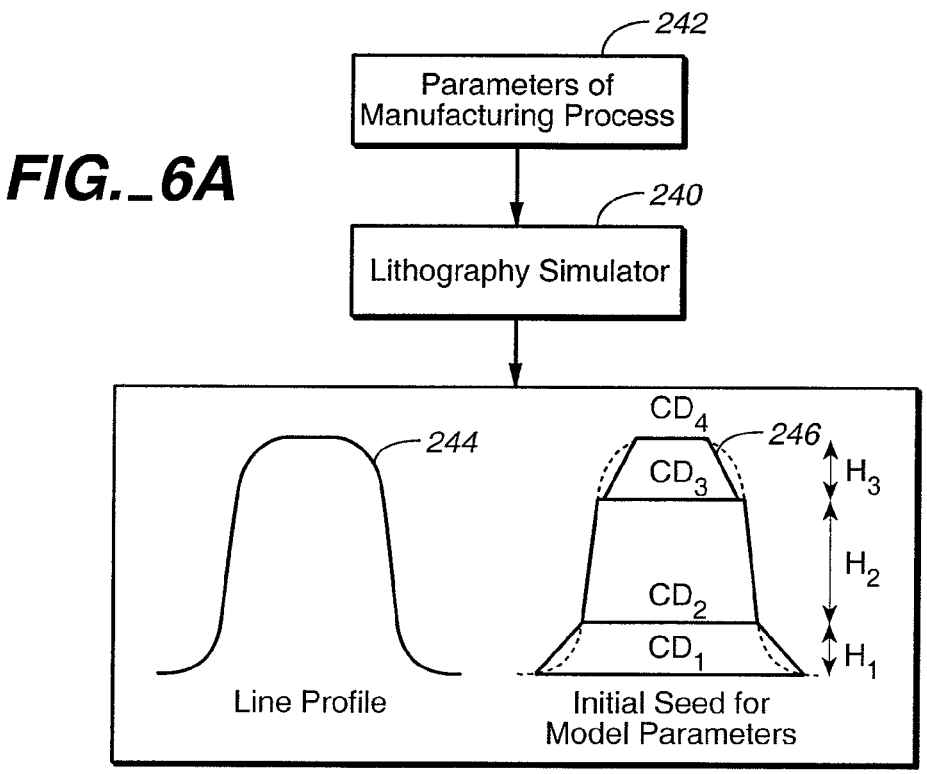
FIG._6A

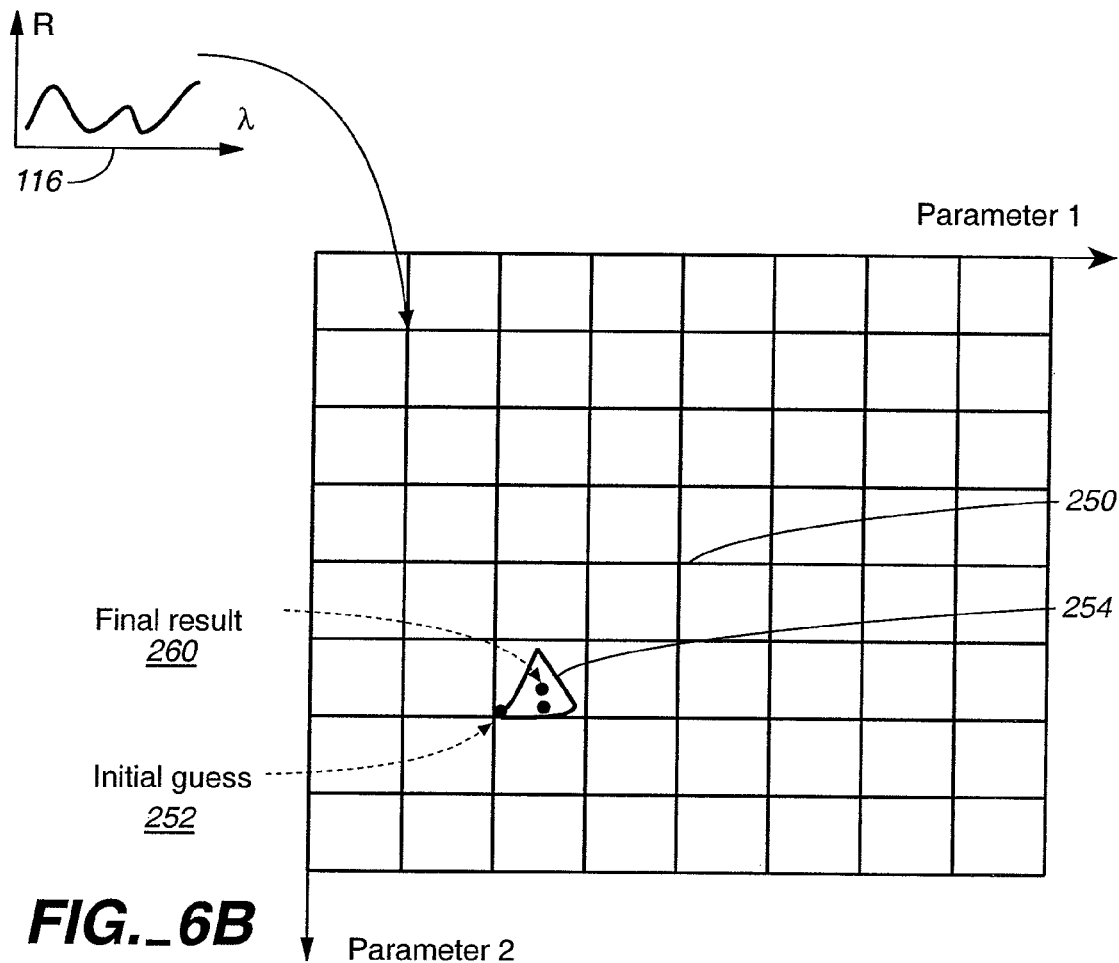
FIG._6B
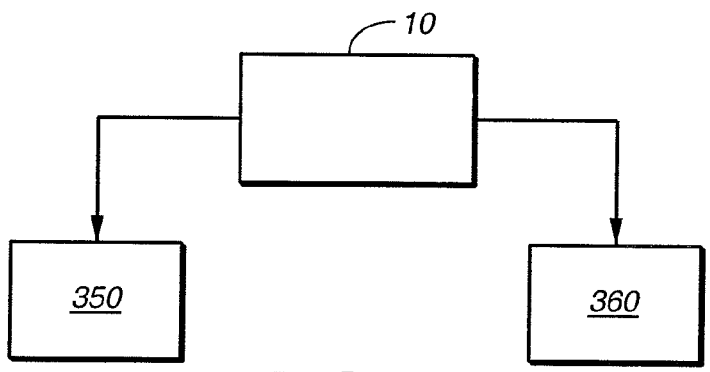
FIG._7

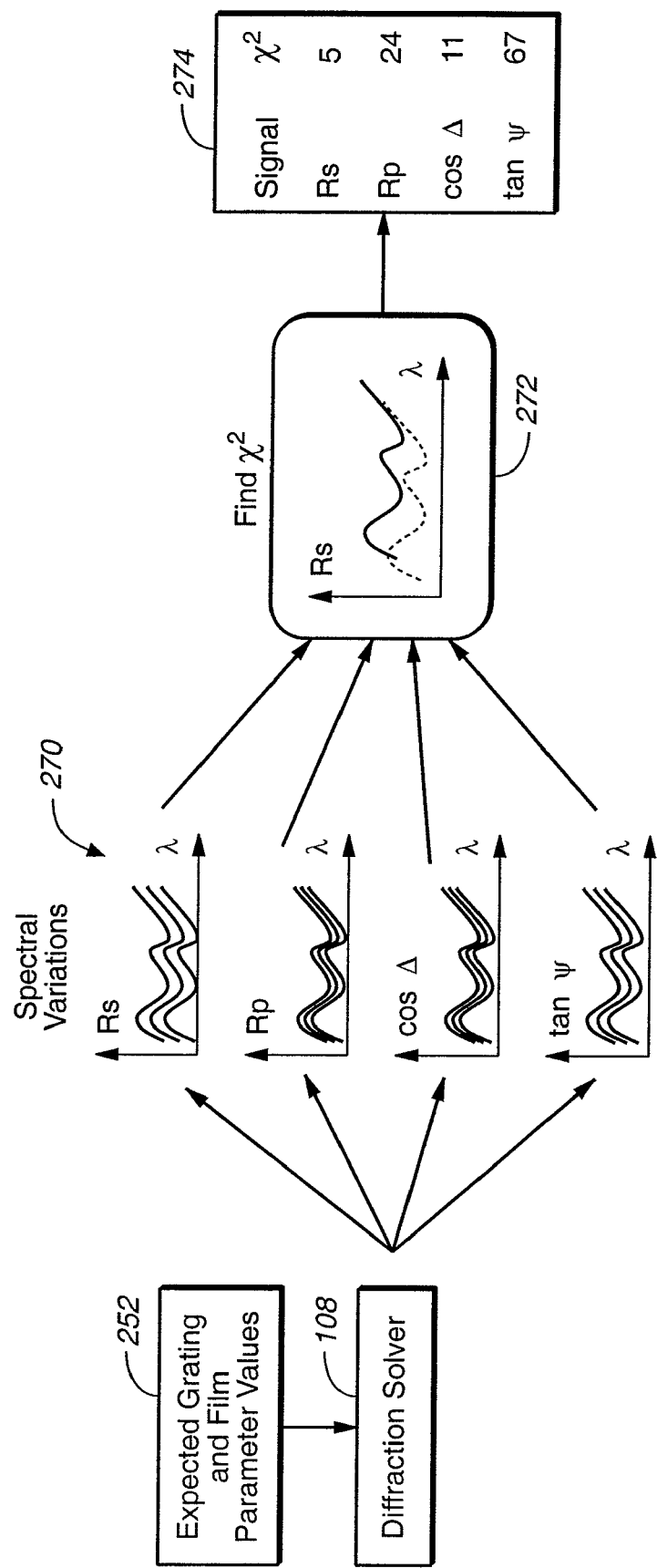
FIG._6C

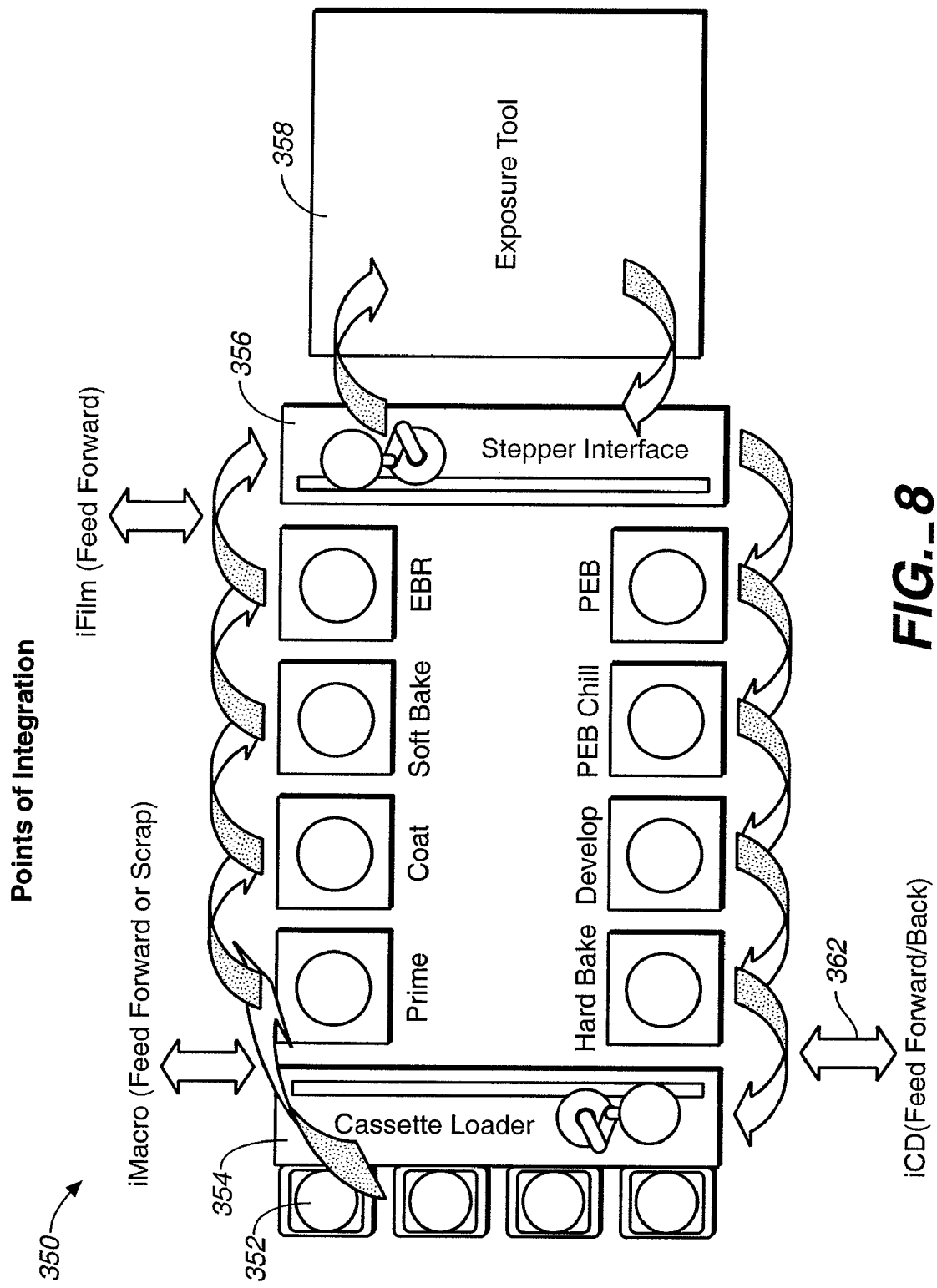
FIG._8

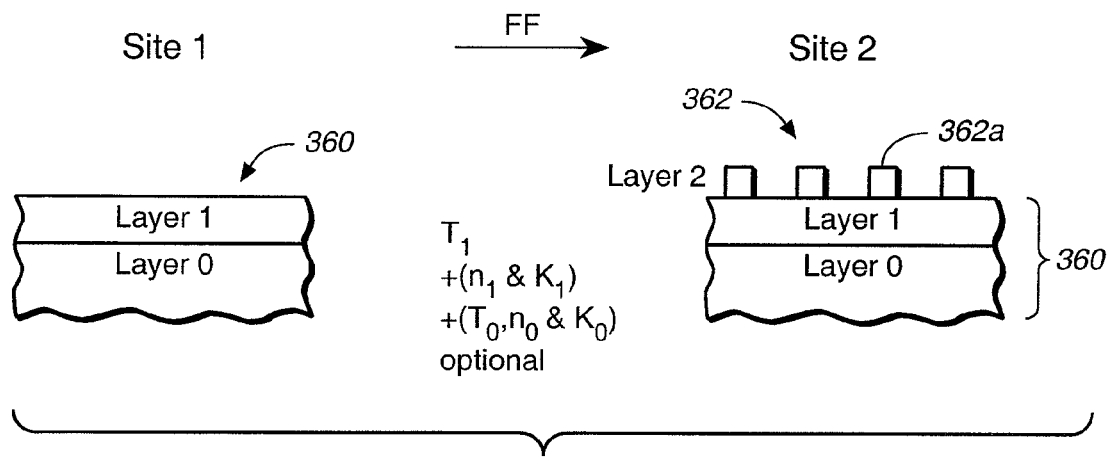
FIG._9A
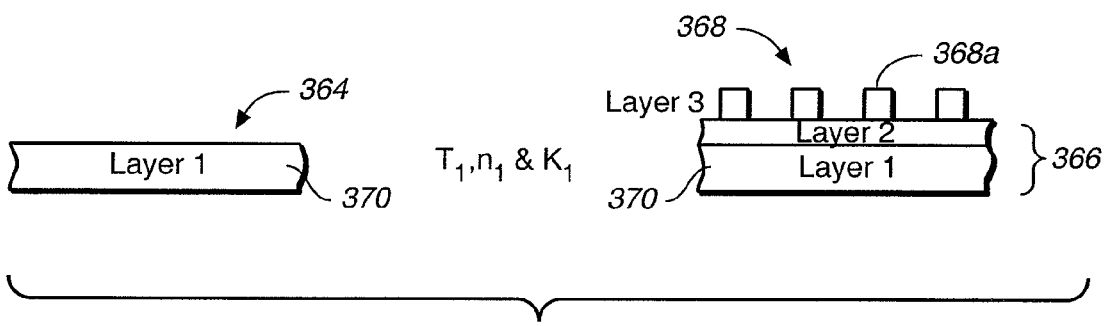
FIG._9B
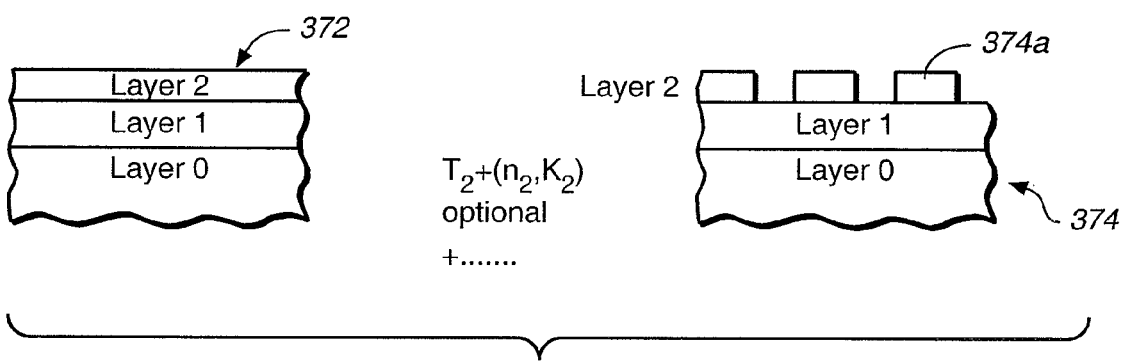
FIG._9C

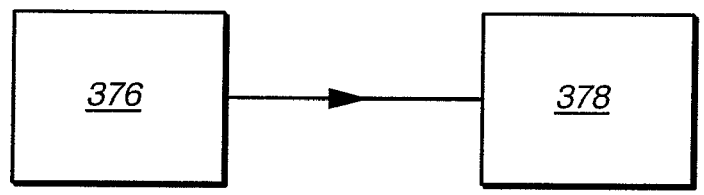
FIG._10
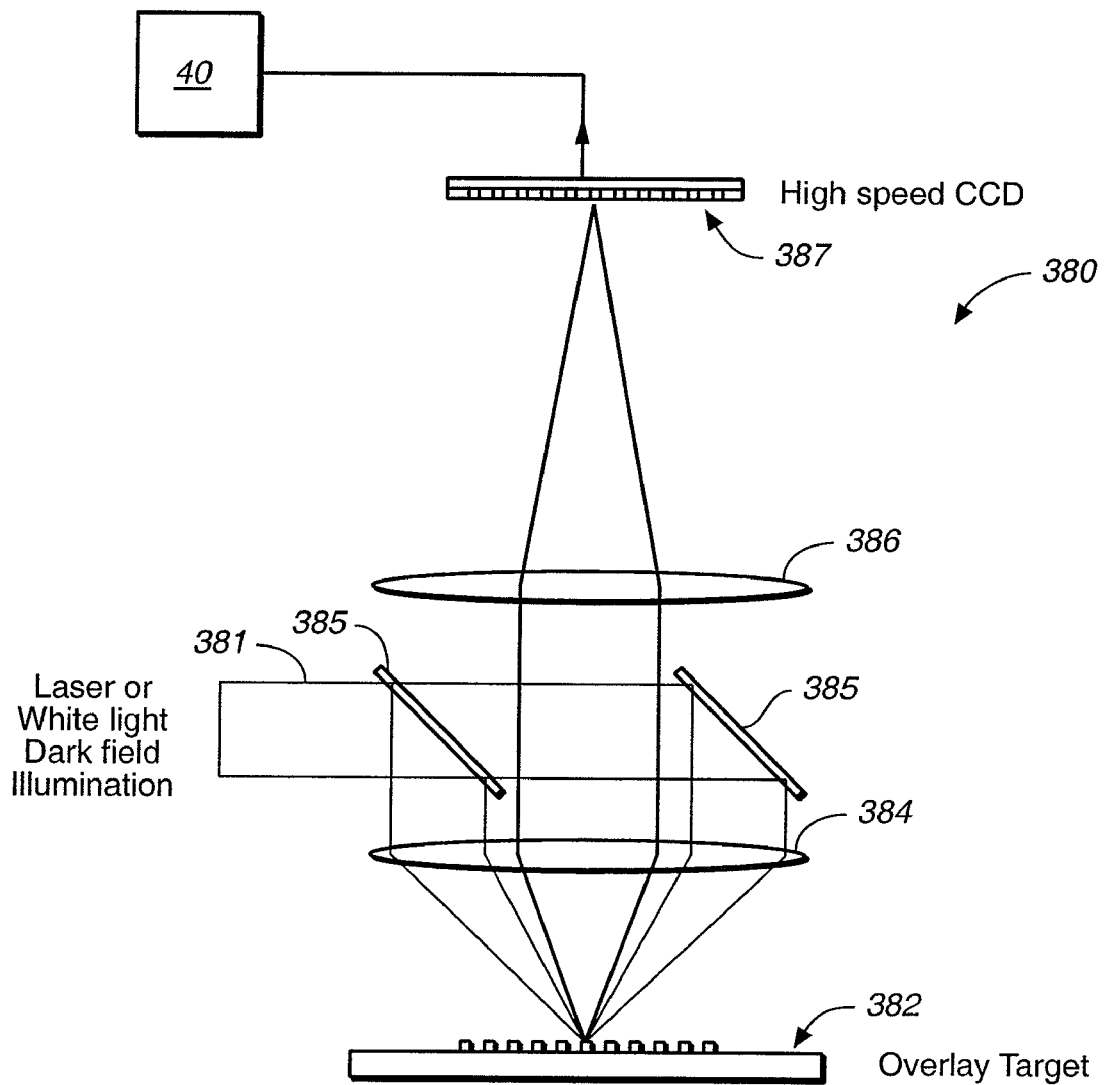
FIG._11

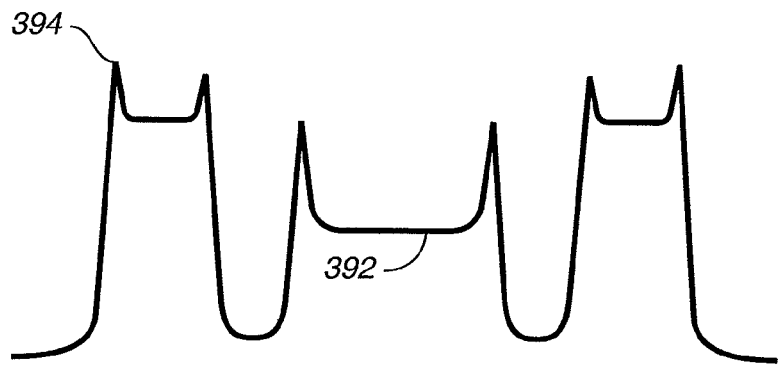
FIG._12
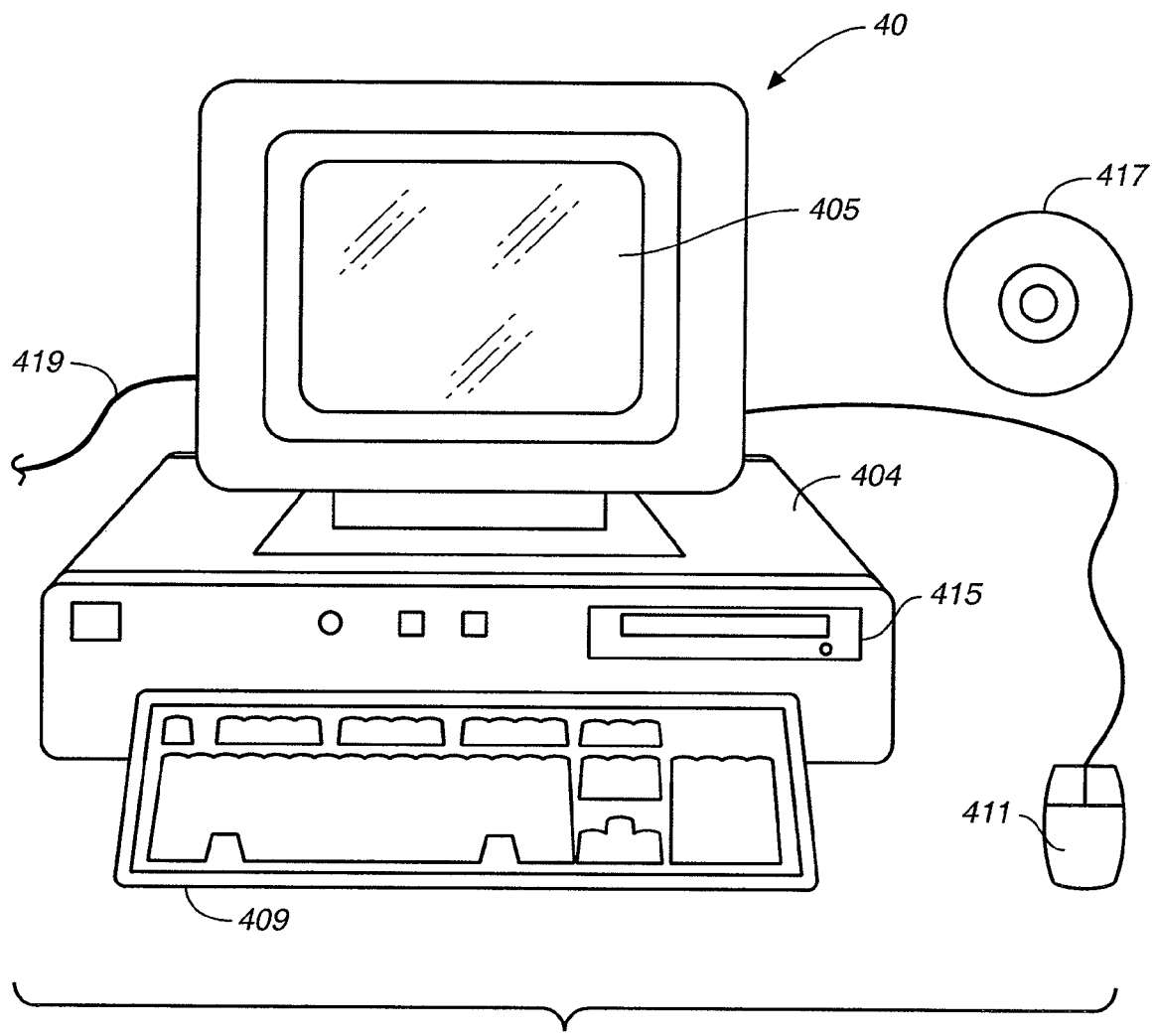
FIG._13

PARAMETRIC PROFILING USING OPTICAL SPECTROSCOPIC SYSTEMS

CROSS REFERENCE TO RELATED APPLICATION

This application is a continuation of U.S. Non-Provisional application Ser. No. 10/327,466, filed Dec. 19, 2002, which in turn claims the benefit of U.S. Provisional Application No. 60/343,077, filed Dec. 19, 2001, which are incorporated herein by reference in their entirety.

BACKGROUND OF THE INVENTION

This invention relates in general to systems for finding profiles of topographical features of small dimensions, such as those of a diffracting grating, and in particular to such systems using optical spectroscopic techniques.

As the integration density and speed of microelectronic devices increase, circuit structures continue to shrink in dimension size and to improve in terms of profile edge sharpness. The fabrication of state-of-the-art devices requires a considerable number of process steps. It is becoming increasingly important to have an accurate measurement of submicron linewidth and quantitative description of the profile of the etched structures on a pattern wafer at each process step. Furthermore, there is a growing need for wafer process monitoring and close-loop control such as focus-exposure control in photolithography.

Spectroscopic diffraction-based techniques are especially well suited for microelectronics metrology applications because they are nondestructive, sufficiently accurate, repeatable, rapid, simple and inexpensive relative to critical dimension-scanning electron microscopy. In such diffraction-based analysis techniques, typically a model of the profile is first constructed, where the model includes a number of parameters that can be varied. One or more diffraction intensity versus wavelength curves are calculated based on the model constructed and the curve(s) are compared with measured diffraction data from the sample. The parameters are then adjusted until a match is found between the curve(s) and the measured data.

The current methods being used include multi-slab models where a number of rectangular or trapezoidal slabs are put on top of one another to form a seed profile that is an approximation of the profile being measured. The parameters that can be adjusted include width and height of the rectangles or width, height and sidewall angle of the trapezoids. It is found that in the wafer processing processes, a number of very different profiles of structures may be encountered. The current methods are inadequate for measuring a wide variety of very different profiles in the manufacturing process. A simple increase of the number of slabs to model such variety of profiles requires the generation of huge libraries whose size grows exponentially with the number of slabs and the associated parameters. Furthermore, different sets of parameters, corresponding to different profiles, can produce indistinguishable spectroscopic data, resulting in a problem known as cross-correlation.

In U.S. Pat. No. 5,963,329, Conrad et al. proposed an improved method to measure actual profiles. In this model, the number of independent parameters or variables is reduced by adopting particular profile shapes such as a "S" line profile, by dividing the model line profile into two or more sub-profiles and providing a numerical model of each sub-profile so that fewer scaling factors may be used to adjust all slab widths and heights within the single sub-profile.

While the above-described method of Conrad et al. reduces the number of parameters that one needs to contend with, this method still has some drawbacks. Thus, it cannot be used for measuring line profiles made of more than material, and for measuring optical parameters as well as geometric parameters. It is therefore desirable to provide an improved model that can be used for determining the above mentioned samples in a manner so that the solution converges to a single solution without a high risk of cross-correlation.

As noted above, the shapes of line profiles encountered on semiconductor wafers during fabrication can take on a wide variety of shapes. Such line profiles are typically situated on and/or below layers of materials which may be the same as or different from the material of the profiles. When diffraction-based spectroscopic techniques are used to measure such profiles, the radiation used in the technique would interact with the one or more layers and transmitted or reflected radiation from the layers is detected by the detectors that are used for detecting radiation from the line profile. Where it is not possible or very difficult to separate the contribution of the signal due to the layers from the contribution of the signal due to the line profile, it is desirable for any technique used to measure the parameters of such layers simultaneously with measurement of the line profile. None of the existing techniques has such capability. It is therefore desirable to provide an improved system where the contribution of such layers to the detector signal can be taken into account.

Currently in the market the common methods of determining a profile (cross section) of a structure are: scanning electron microscopy or SEM (cross section and top down), atomic force microscopy or AFM, and scatterometry. For production monitoring scatterometry is being established as the leading method for lot by lot monitoring using periodic test targets.

The basic methodology in scatterometry is the comparison of the measured (typically spectral) data to a library that has been prepared in advance and contains the possible variations of the target profile AND underlying layers. However, in many situations the number of variables (e.g. underlying layer thickness in a damascene layer) is prohibitively large and therefore prevent the user from creating a library.

U.S. Pat. No. 5,963,329 describes the use of a real time regression algorithm for the determination of the grating profile using its measured spectral reflected intensity. A major difficulty with this algorithm is that the regression time becomes prohibitive for more than 4 degrees of freedom (floating parameters such as the CD, side wall angle and underlying film thickness). This prevents the user from using this methodology for the measurements of damascene structures or even photo-resist on complex/variable films. In addition, the added number of degrees of freedom results in a non-robust root convergence that will tend to lock onto local correlated minima.

The major disadvantages of the above methods are as follows. It is difficult to create a library for gratings on multi variable films (e.g. photo resist on damascene layer or etched trenches or vias in inter-metal dielectrics). It is also difficult to regress in real time on more than 4 floating profile and film variables. It is therefore desirable to provide an improved system to alleviate such problems.

SUMMARY OF THE INVENTION

Semiconductor devices are fabricated by processing equipment with certain set parameters of the manufacturing process, such as the time, temperature, focus and exposure dose in the lithography and other parameters, such as the time and temperature for the deposition of certain layers, or the time, and nature of etching processes. Once these parameters are known, it is possible to simulate the profile of the structures that will result from such manufacturing process. A gallery of seed profiles or profile types may be used as possible starting points for finding the actual shapes of line profiles. Preferably, knowledge of manufacturing process parameters may be utilized in the construction of a gallery of profile types from which a particular profile type can be chosen for matching with the measured data. Also preferably, knowledge of manufacturing process parameters is utilized to select from the gallery a particular profile type that would serve as the best seed profile for the purpose of finding the actual profile of structures.

As noted above, the diffracting structure to be measured is frequently located on and/or below one or more layers of the same or different material, so that the detector employed would detect radiation influenced by such layers as well as diffraction from the diffracting structure. These layers would have to be taken into account in the model. Parameters such as thickness and index of refraction (n and k) of these layers would be more sensitive to certain measurement parameters than others. This is also true of the parameters characterizing the diffracting structure. Therefore, in another embodiment of the invention, more than one set of radiation data may be generated from each profile type, where the sets of radiation data generated are of different radiation parameters, such as reflectance or transmittance parameters and ellipsometric parameters. For a given change in the parameter of the profile type (e.g., width, height, sidewall angle, index of refraction of the diffracting structure and thickness and index of refraction of the one or more layers) may be more sensitive to the ellipsometric parameters than to the transmittance or reflectance parameters, or vice versa. In such event, it may be desirable to choose the set of radiation data and the associated radiation parameters that are more sensitive to a change in the parameter of the profile or a characteristic of the one or more layers to improve the accuracy and precision of the modeling and matching algorithm. This feature can also be used where the effects of the layers need not be taken into account, such as where the effects are known, can be ignored or where there is no layer associated with the structure.

Independent of the above considerations, reflectance or transmittance parameters and ellipsometric parameters of the collected radiation may be used together for deriving one or more parameters of a profile with arbitrary shape.

The gallery of profile types may be stored in a database made available to users and an optional processor may be used to select the profile type from the gallery and compare the detected measured data to that associated with the selected profile type to arrive at a set of values of the one or more parameters of the profile type.

Where the profiles measured are useful for controlling a wafer manufacturing process, the measured information may be used to control the processing system for adjusting one or more processing parameters. Thus, if the profile of the structure measured indicates a problem in the processing system, the processing system may be adjusted to reduce or eliminate the effects of the problem. Any one of the above-described techniques may be used to find a profile of a structure and/or characteristics of one or more layers in the vicinity of the structure, and these values may then be supplied to a semiconductor wafer processing machine, such as a track, stepper and/or etcher, to control the lithographic and/or etching process in order to compensate for any errors in one or more parameters of the profile that has been discovered. The track, stepper and/or etcher may form a single tool with a system for finding the one or more parameters of a profile, or may be instruments separate from it.

To reduce the complexity in determining parameters such as the critical dimension, side wall angle and thickness of scattering and diffracting structures and of the properties of film stacks above and/or below the scattering and diffracting structures, multiple measurements may be combined. Thus, in order to simplify the method for determining one or more parameters of a diffracting structure, a reference structure may be measured where the reference structure comprises at least one layer that has substantially the same thickness as the diffracting structure, and/or comprises a material having substantially the same optical properties as those of a material in the diffracting structure. Information so obtained concerning the reference structure may then be used to simplify the determination of the parameters of the diffracting structure.

Where the diffracting structure is located adjacent to one or more films, the reference structure may also be located adjacent to a film structure than contains one or more layers whose properties are similar to those of one or more films adjacent to the diffracting structure. Therefore, by measuring the reference structure together with the properties of layers adjacent to it, the information so obtained on the properties of the layer(s) with similar properties can be used for determining the parameter values of the diffracting structure.

The reference structure may be a smooth or diffracting structure on the same sample as the diffracting structure and the films associated with the reference structure may be formed in the same processing steps as the film structure adjacent to the diffracting structure, so that both the diffracting and reference structures are situated adjacent to two different film stacks with the same properties.

Where two diffracting structures are present on the same sample, or on different samples of the same lots made by the same processing steps, to simplify the profile measurement of the structures, the profile obtained from one diffracting structure may be used as the seed profile in an optimization process for determining the parameters of another diffracting structure.

Information obtained by a scatterometric measurement may be fed to a critical dimension-scanning electron microscope measurement (CD-SEM) on the same target, or a different target on the same wafer or on a different wafer in the same lot made by the same processing process. The use of scatterometric data would help eliminate uncertainty that exists in scanning electron microscope algorithms with respect to the wall angle dependence of critical dimension measurements, and provides an absolute calibration of the pitch for the scanning electron microscope elements.

Scatterometric measurement data may also be fed to an overlay measurement tool on the same target or a different target on the same wafer, or on a different wafer but in the same lot produced by the same process. The use of scatterometric data would assist in eliminating the uncertainty that would exist in overlay algorithms caused by the profiles of the target.

In some measurements, it may not be possible to obtain the properties of film stacks over and/or below the diffracting structure. In such event, it may be desirable to determine the profile of the structure by using only a portion of the collected data, or the data of one of the parameters associated with the diffracting structure, where the influence of the film stack on measurements of the diffracting structure is minimized. In other words, the subset of data of the parameters and/or the parameter(s) used in the optimization process would be selected to minimize the effect of the films stack on the optimization process.

While the above-described features may be implemented as a stand-alone system and integrated with optical equipment for carrying out the measurements, it is possible for existing optical measurement equipment to be modified or otherwise enabled so that it has the capability described above. Thus, the above-described features may be embodied as a program of instructions executable by computer to perform the above-described different aspects of the invention. Hence any of the techniques described above may be performed by means of software components loaded into a computer or any other information appliance or digital device. When so enabled, the computer, appliance or device may then perform the above-described techniques to assist the finding of value(s) of the one or more parameters using measured data from a diffracting structure and/or the associated one or more layers. The software component may be loaded from a fixed media or accessed through a communication medium such as the internet or any other type of computer network.

Each of the inventive features described above may be used individually or in combination in different arrangements. All such combinations and variations are within the scope of the invention.

BRIEF DESCRIPTION OF THE DRAWINGS

FIG. 1A is a schematic view of a spectroscopic measurement device useful for illustrating the invention.

FIG. 1B is a cross-sectional view of a two-dimensional grating and associated layers useful for illustrating the invention.

FIG. 2 is a schematic view of another spectroscopic measurement device useful for illustrating the invention.

FIGS. 3A, 3B, 3C are cross-sectional views of two-dimensional structures encountered in semiconductor manufacturing useful for illustrating the invention.

FIG. 3D is a perspective view of a three dimensional periodic structure with via holes useful for illustrating the invention.

FIGS. 4A-4F are sample profiles to illustrate a gallery of profile types or models to illustrate an embodiment of the invention.

FIG. 5A is a flow chart of profile and film measurement to illustrate an embodiment of the invention.

FIG. 5B is a flow chart illustrating in more detail the diffraction solver in the flow chart of FIG. 5A.

FIG. 6A is a flow chart illustrating the selection of the optimum profile type or model and the value of parameters for the initial seat values.

FIG. 6B is a flow chart illustrating the process for selecting the optimal radiation parameter and the corresponding set of radiation data for matching with measured data to illustrate one aspect of the invention.

FIG. 6C is a schematic diagram illustrating the selection of the starting point for nonlinear optimization from a course library to illustrate an aspect of the invention.

FIG. 7 is a schematic block diagram illustrating a wafer processing apparatus including a track/stepper and an etcher and a spectroscopic measurement device where information from a diffracting structure and/or associated structures from the device as used to control the manufacturing process and the track, stepper and/or etcher to illustrate the invention.

FIG. 8 is a schematic block diagram illustrating in more detail the track/stepper of FIG. 7.

FIGS. 9A, 9B, 9C are schematic views of sample structures useful for illustrating different embodiments of the invention for determining the profile or parameters of a diffracting structure.

FIG. 10 illustrates an embodiment where data obtained from a scatterometric measurement tool is fed forward to a CD-SEM measurement or overlay tool performing a measurement on the same target or a target with some common features.

FIG. 11 is a schematic view of an overlay tool measuring the offset between two gratings to illustrate a feature of the invention of FIG. 10.

FIG. 12 is a one-dimensional image of a box-in-box type target to illustrate a feature of the invention of FIG. 10.

FIG. 13 is a block diagram showing a representative sample logic device in which aspects of the present invention may be embodied.

For simplicity and description, identical components are labeled by the same numerals in this application.

DETAILED DESCRIPTION OF THE EMBODIMENTS

Even though much of the description below of algorithms and methods are described in terms of the reflected or transmitted intensities of the diffraction caused by the diffracting structure, it will be understood that the same techniques and algorithms may be used for data containing information concerning changes in the polarization state over different wavelengths (e.g. ellipsometric parameters $\Delta$ and $\Psi$ as functions of wavelength). For this reason, it may be advantageous to employ an instrument which is capable of measuring both the reflected or transmitted intensities of the diffraction caused by the structure as well as changes in polarization state caused by the diffraction of the structure. A suitable system is described below in reference to FIG. 1A.

FIG. 1A is a schematic view of a spectroscopic diffraction-based metrology system to illustrate the preferred embodiment of the invention. As shown in FIG. 1A, system 10 may be used to measure reflected or transmitted intensities or changes in polarization states of the diffraction. As shown in FIG. 1A, a semiconductor wafer 11 may comprise a silicon substrate 12, and a structure 16 thereon that may include a photoresist pattern on and/or over film stack(s), where the film(s) are at least partially light-transmissive and has a certain film thickness and refractive index (n and k, the real and imaginary components of the index).

An XYZ stage 14 is used for moving the wafer in the horizontal XY directions. Stage 14 may also be used to adjust the z height of the wafer 11. A polychromatic or broadband radiation source such as white light source 22 supplies light through a fiber optic cable 24 which randomizes the polarization and creates a uniform light source for illuminating the wafer. Preferably, source 22 supplies electromagnetic radiation having wavelengths in the range of at least 180 to 800 nm. Upon emerging from fiber 24, the radiation passes through an optical illuminator 26 that may include an aperture and a focusing lens or mirror (not shown). The aperture causes the emerging light beam to illuminate an area of structure 16. The light emerging from illuminator 26 is polarized by a polarizer 28 to produce a polarized sampling beam 30 illuminating the structure 16.

The radiation originating from sampling beam 30 is reflected by structure 16, passed through an analyzer 32 and to a spectrometer 34 to detect different spectral components of the reflected radiation, such as those in the spectrum of the radiation source 22, to obtain a signature of the structure. In one mode (spectrophotometry mode) of operation, the reflected intensities are then used in a manner described below to find the value(s) of one or more parameters of structure 16. The system 10 can also be modified by placing the spectrometer 34 on the side of structure 16 opposite to illumination beam 30 to measure the intensities of radiation transmitted through structure 16 instead for the same purpose. These reflected or transmitted intensity components are supplied to computer 40.

Alternatively, the light reflected by the structure 16 is collected by lens 54, and passes through the beam splitter 52 to a spectrometer 60. The spectral components at different wavelengths measured are detected and signals representing such components are supplied to computer 40. The light reflected by structure 16 may be supplied by source 22 through illuminator 26 as described above or through other optical components in another arrangement. Thus, in such arrangement, lens 23 collects and directs radiation from source 22 to a beam splitter 52, which reflects part of the incoming beam towards the focus lens 54 which focuses the radiation to structure 16. The light reflected by the structure 16 is collected by lens 54, passes through the beam splitter 52 to spectrometer 60.

When the system 10 is operated in another mode (spectroscopic ellipsometry mode) used to measure the changes in polarization state caused by the diffraction by the structure, either the polarizer 28 or the analyzer 32 is rotated (to cause relative rotational motion between the polarizer and the analyzer) when spectrometer 34 is detecting the diffracted radiation from structure 16 at a plurality of wavelengths, such as those in the spectrum of the radiation source 22, where the rotation is controlled (not shown) by computer 40 in a manner known to those skilled in the art. The diffracted intensities at different wavelengths detected are supplied to computer 40, which derives the changes in polarization state data at different wavelengths from the intensities in a manner known to those in the art. See for example U.S. Pat. No. 5,608,526, which is incorporated herein by reference.

FIG. 1B is a cross-sectional view of the structure 16 on substrate 12, which structure comprises a diffracting structure 16b situated between the film stack 16a above the structure and the film stack 16c underneath the structure and an incident electromagnetic beam 30 to illustrate the invention. Thus, the incident beam 30 of the electromagnetic radiation first encounters the interface between the air and the film stack 16a and interfaces that may be present within the stack. Next, the portion of the radiation from beam 30 that penetrates the film stack 16a is diffracted by the grating structure 16b. At least some of the radiation from beam 30 will reach the film stack 16c underneath the grating and be reflected by or transmitted through interfaces associated with stack 16c. The total light reflectance is affected both by the grating and by the film stacks above and/or below the grating. Multi-layer interference, caused by multiple reflections between the films and the grating, creates a complicated pattern in a reflectance spectrum, which can be used for measuring parameters of the structure. A part of radiation from beam 30 that is not reflected or diffracted as described above will be transmitted into the substrate 12. As shown in FIG. 1B, the grating 16b has a height of H, a critical dimension ("CD") and a sidewall angle (SWA) as indicated.

FIG. 2 is a schematic view of an alternative spectroscopic measurement system 80 to illustrate the invention. The system of FIG. 2 differs from that in FIG. 1A in that it uses the same optical components for both the spectrophotometry mode measurement as well as the ellipsometry measurement, and thus has fewer optical components. On the other hand, the two modes need to be employed sequentially and not simultaneously as is possible with the apparatus of FIG. 1A. As before, where there is relative rotational motion between the polarizer 28 and analyzer 32 when a measurement is taken, the system 80 of FIG. 2 operates as an ellipsometer. This can be achieved by rotating either the polarizer 28 or the analyzer 32, or both. Where there is no relative rotation between polarizer 28 and analyzer 32 (such as where both did not rotate, or rotate at the same speed), instrument 80 operates as a spectrophotometer or reflectometer.

As shown in FIG. 2, system 80 further includes a beam divider 82 which diverts the portion of the illumination beam from source 22 to a spectrometer 84 which measures variations in the intensity of the illumination beam so that the effects of such variations may be removed from the measurements. Beam shaping optics 86 is employed to shape the illumination beam, such as by collimating or focusing the beam.

While some diffracting structures may take on simple geometric shapes such as that illustrated in FIG. 1B, in some instances, these structures can take on more complex shapes. When this is the case, it is desirable to provide a model by which a much wider variety of profiles of structures can be predicted than can conventional models. FIGS. 3A-3D illustrate the type of structures that may be encountered during the wafer manufacturing process. FIG. 3A is a cross-sectional view of a line grating on top of a film stack, where the cross-section of each line is in the shape of a trapezoid 92, and the film stack comprises layers 94a (bottom anti-reflection coating, or BARC), 94b (polysilicon), 94c (silicon dioxide) on top of a substrate 12.

Alternatively, the structure may comprise periodic lines where each line comprises a stack of several different materials, where the cross-sectional shape of the lines is curved. As illustrated in FIG. 3B, the diffracting structure comprises three layers: 96a, 96b, 96c and the diffracting structure is located on top of a film 94 which may comprise one or more layers. The structure in FIG. 3B typically results from the process of shallow trench isolation ("STI"). Yet another example of a realistic structure encountered in wafer manufacturing is illustrated in FIG. 3C which comprises a line grating with sidewall spacers, made of a material different form that of the line grating. As shown in FIG. 3C, each line grating comprises a center portion 98a which is substantially rectangular in cross-section and two sidewalls 98a, 98b on the two sides of the rectangle where the line structures are situated on top of a film 94. The sidewall spacers of FIG. 3C are typically used to control the desired shape of polysilicon lines 98 in the process of reactive ion etching ("RIE").

FIG. 3D is a perspective view of a periodic structure with via holes where the holes may penetrate one or more layers. The via holes provide vertical connections from one metallization layer to another. Thus, the structure 16 of FIGS. 1A, 2 may include one or more of the diffracting structures and layers shown in FIG. 1B, 3A-3D. From the shapes of the structures illustrated in FIGS. 3A-3D, it will be evident that prior art methods, such as the one described in U.S. Pat. No. 5,963,329, may be inadequate for measuring the more complex structures illustrated in such figures.

FIG. 4A-4F illustrate examples of profile models which may advantageously serve as the seed profiles or profile types that may be employed to derive the actual profile of a diffraction structure encountered in semiconductor manufacturing. FIG. 4A illustrates a cross-sectional view of a profile type comprising a single-material, multi-trapezoid profile, characterized by values of CD, height and sidewall angle for each trapezoid. When the sidewall angles are fixed at 90 degrees, this profile type becomes a multi-slab model. The bottom trapezoid models a footer.

FIG. 4B is a cross-sectional view of a single-material, quartic profile which may be represented by the polynomial expression $y=ax^4$, characterized by the height of the profile and coefficient value a. FIG. 4C is a cross-sectional view of a single-material, quartic profile with a bottom rounding (i.e., rounded footer), characterized by height, quartic coefficient a and parameters of the bottom rounding or footer. More than one model may be used for the footer, one example being a model using a smooth function (e.g. straight line as shown in FIG. 4A, or curved line such as that of a quadratic function). FIG. 4D is a cross-sectional view of a multi-material, etched quartic profile of the form $y=ax^4$, characterized by coefficient a and the thicknesses of each of the three layers. FIG. 4E is a cross-sectional view of a two-material profile with sidewall spacers, characterized by height, edge and profiling parameters for the inner and outer materials of the spacers, such as common height value for the inner and outer materials, different CD values for the inner and outer materials, and a sidewall angle for the outer material. FIG. 4F is a perspective view of a three-dimensional structure with the via hole profile in a uniform layer, characterized by the height and hole parameters (radius for a circular hole).

While the quartic profile is illustrated in FIGS. 4B, 4C and 4D, profiles that can be described using other polynomial expressions may also be used and are within the scope of the invention, such as quadratic parabolas, or a combination of quartic and quadratic parabolas. In the same vein, while the profile type in FIG. 4A includes multiple slabs that are trapezoidal, slabs defined by one or more analytical functions, such as where one side of the trapezoid is curved, may be employed and are within the scope of the invention.

The profile types in FIGS. 4A-4F do not include layers of material which may lie above and/or below the actual diffracting structures measured. These layers can also be modeled as described below using parameters for such layers, such as thicknesses and indices of refraction (referred to herein also as film parameters), so that the models constructed using the profile types can take into account the layers above and/or below the diffracting structures measured. In addition, the profile types themselves may include layers, such as those illustrated in FIG. 4D. The layers of the profile type in FIG. 4A can be modeled using not only geometric parameters, such as the coefficient a and height of each of the three layers, but also the complex index of refraction of each of the materials in the three layers of the profile itself.

Before any measurement of structure 16 is made using the apparatuses in FIGS. 1A and 2, a gallery of profile types such as those illustrated in FIGS. 4A-4F is first prepared and stored in the database. FIG. 5A is a flowchart of profile and film measurement to illustrate a process using a model to measure the parameters of the diffracting structure. Where the structure is situated on and/or below one or more layers of materials, the model may also be used to measure one or more parameters of such layers. As shown in FIG. 5A, an off-line pre-processing tool 102 is used to provide the gallery described above together with the seed profile and film parameters associated with each of the profile types, such as the profile types illustrated in FIGS. 4A-4F, together with layers over and below the profiles shown. The profile parameters can include, for example, CD, height, sidewall angle, parameters associated with polynomial expressions such as the coefficient a and height of quartic profiles, parameters of the bottom rounding and of the spacers, and the indices of refraction (n and k) parameters of materials of the line profile. The film parameters may include thicknesses of the layers and the indices of refraction (n and k).

Tool 102 then computes from the profile types and their associated profile and film parameters, as well as initial values of such parameters (e.g. based on estimation, or the knowledge or simulation of the fabrication process), predicted spectra radiation data associated therewith in a diffraction solver 108. The operation of the diffraction solver 108 is illustrated in more detail in FIG. 5B. As shown in FIG. 5B, the profile type may be approximated by slabs (block 110). Eignvalues and S-matrices for each slab and each film underneath and/or over the profile type are computed (block 112). S-matrices are then propagated (block 114) to arrive at a spectrum (block 116), which is the predicted radiation data when a profile is measured using the instruments of FIGS. 1A, 2. For a detailed description of the modeling process applied by solver 108, please see the references below:

M. G. Moharam, E. B. Grann, D. A. Pommet, and T. K. Gaylord, "Formulation of stable and efficient implementation of the rigorous coupled-wave analysis of binary gratings," J. Opt. Soc. Am. A, vol. 12, pp. 1068-1076 (1995);

L. Li, "Formulation and comparison of two recursive matrix algorithms for modeling layered diffraction gratings," J. Opt. Soc. Am. A, vol. 13, pp. 1024-1035 (1996); and M. G. Moharam, "Coupled-wave analysis of Two-Dimensional Dielectric Gratings," PROC. SPIE, vol. 883, pp. 8-11 (1988).

Returning now to FIG. 5A, the spectra associated with the actual diffracting structure and the film(s) in structure 16 are then measured using the apparatus of either FIG. 1A or FIG. 2 (block 120) or any other suitable apparatus and the measured data is then compared with the predicted spectrum from the diffraction solver 108 (block 122). If there is a good match between the two spectra, the initial values of the parameters of the profile type and of the film(s) then correctly predict those of the actual structure and film(s) that are measured (block 124). If the match is less than satisfactory (block 126), the profile and film parameters (block 106) are then varied or adjusted by means of a nonlinear optimization tool (block 126) in a feed back path. The steps of the diffraction solver 108 and the comparison 122 are repeated until there is a satisfactory match between the predicted spectrum and the experimental spectrum. Any number of nonlinear optimization tools may be employed, such as those described in the following articles:

J. Nocedal and S. J. Wright, "Numerical Optimization," Springer-Verlag, New York, N.Y. (1999); and D. T. Pham and D. Karaboga, "Intelligent Optimization Techniques: Genetic Algorithms, Tabu Search, Simulated Annealing and Neural Networks," Springer-Verlag, New York, N.Y. (2000).

As described above in reference to FIGS. 3A-3D, the actual diffracting structures encountered in wafer processing include a wide variety of different shapes. According to one aspect of the invention, information concerning the manufacturing process may be advantageously used in selecting profile types for the gallery which serve as the seed profiles for the modeling process. Thus, the gallery of FIGS. 4A-4F are selected keeping in mind the structures encountered in semiconductor manufacturing, such as those in FIGS. 3A-3D.

As noted above, semiconductor devices are fabricated by processing equipment with certain set parameters of the manufacturing process, such as the time, temperature, focus and exposure dose in the lithography and other parameters for deposition of certain layers or of etching processes. Once these parameters are known, it is possible to derive the profile of the structures that will result from such manufacturing process. A software tool that may be used to simulate the profile of the structures resulting from the manufacturing process is PROLITH™ simulator software, available from KLA-Tencor Corporation, the assignee of the present application, in San Jose, Calif. This software is described in *Inside PROLITH*, by Chris A. Mack, Finle Technologies (Austin, Tex.: 1997). Another possible tool that may be used to simulate the profile of the structures resulting from the manufacturing process is Solid_C, from Sigma_C, Munich, Germany. Thus, once information concerning the manufacturing process, such as the values of the manufacturing process parameters (e.g., time, temperature) is available, the profile that is predicted from such parameters may then be used to select a profile type from the gallery of profile types to serve as the seed profile for the modeling process illustrated in FIGS. 5A, 5B. In addition, the predicted profile arrived at using manufacturing process information may also be used to select a set of initial values of the parameters associated with the profile type, such as initial values of CD, sidewall angle, height, coefficient a and height of quadric expressions or coefficients of other polynomial-type expressions, and a process window in which these parameters are expected to vary. This process is illustrated in FIG. 6A.

As illustrated in FIG. 6A, a lithography simulator 240 (e.g. PROLITH™ simulator) simulates, from parameters of manufacturing process 242, a line profile 244. From the simulated line profile 244, the profile type of FIG. 4A in the gallery that is the closest match to line profile 244 is then selected as the seed profile. The line profile 244 is also used to select initial values of the different parameters of such profile type, so that the predicted profile using such profile type is the closest match to simulated profile 244. Thus, in the example in FIG. 6A, initial values of the seven parameters $CD_1$, $CD_2$, $CD_3$, $CD_4$ and $H_1$, $H_2$, $H_3$ are selected for the modeling process of FIGS. 5A, 5B so that the predicted profile 246 shown in FIG. 6A is the closest match to simulated profile 244. By making use of the manufacturing process as described above, a profile type with initial parameter values that is close to the actual structure being measured is selected as the seed profile for the modeling process, so that the non-linear optimization process illustrated in FIG. 5A can converge rapidly.

The above-described modeling process starting with the seed profile or profile type and with the initial parameter values is illustrated in FIG. 6B. As noted above, from information available from the manufacturing process, it is possible to ascertain a process window in which parameter values may vary. Such window is illustrated in FIG. 6B, where the ranges of the parameters 1 and 2 shown are the ones through which these two parameters may vary. The window may be defined with respect to a center point 250, and an amount that each parameter is allowed to deviate from the value at this center point; the center point and the deviation allowed for each parameter are derived from the manufacturing information. The process window may be divided into different sections by a set of vertical lines and a set of horizontal lines, where the intersections between the two sets of lines form a set of points, each of which correspond to a pair of values for the two parameters. Solver 108 may be used to derive the radiation spectra corresponding to these pairs of values, where the spectra and their corresponding pairs form a coarse library. Where the profile type is characterized by more than two parameters, the window would be a space with more than two variables, and each intersection point would correspond to a set of more than two parameters.

After this coarse library has been constructed, the spectra in the library are matched with the simulated data to find the closest match. The intersection point 252 corresponding to the closest matching spectrum indicates the set of initial parameter values that is a good starting point to perform the optimization process of FIG. 5A. The line 254 in FIG. 6B illustrates schematically the path taken by the optimization process, arriving at the final result at point 260 in FIG. 6B.

In the profile type of FIG. 4A, for example, there will be at least three parameter values: CD, height ("H") and sidewall angle ("SWA"). For some profile types, two parameters may be adequate, such as the quartic profile type of FIG. 4B, which may be characterized by the coefficient a and height of the profile. As noted above, the set of initial parameter values of the profile type selected is such that the predicted profile using the profile type from the gallery is the closest match to the simulated profile. Thus, as noted above in reference to FIG. 5B, a spectrum or spectra of a radiation parameter over a range of wavelengths 116 is arrived at using the diffraction solver 108 which corresponds to the set of initial values 252 of the profile type selected and its associated films. This spectrum or spectra are then compared with the measured data as in block 122 of FIG. 5A and a non-linear optimization tool may be utilized as described to arrive after convergence, along path 254, at a final set 260 of parameter values of the profile type. If the profile type of FIG. 4A is selected, for example, the final set 260 would comprise the final values of the CD, height and sidewall angle of each trapezoid.

In order to speed up the process described in reference to FIG. 5A, a coarse library such as that indicated in FIG. 6B may be pre-computed off-line, so that each profile type in the gallery is stored together with a number of sets of initial parameter values, such as those corresponding to the intersection points (e.g., 252) in the grid-like structure in FIG. 6B, and their corresponding spectra. The diffraction solver 108 is then used to compute the spectrum corresponding to each of the intersection points and such spectra are stored together with the profile type and the associated sets of initial parameter values at the intersection points. Then, when a simulated profile becomes available, such as simulated profile 244 in FIG. 6A, such simulated profile is then matched against the predicted profiles that correspond to the different sets of initial parameter values corresponding to the intersection points in FIG. 6B in the coarse library. From this comparison, a particular intersection point in the grid-like structure and the corresponding set of initial parameter values may be quickly identified and the process of blocks 120, 122, 124 and 126 of FIG. 5A may be carried out very quickly to locate the final set 260 of parameter values of the profile type. Thus, while the resolution of the coarse library of FIG. 6B is not sufficient for measurement, it provides significant acceleration of non-linear optimization. Where a coarse library is not constructed before hand, the center point 250, its corresponding set of parameter values and spectra, may be used as the starting point for the optimization process in FIG. 5A.

The above-described radiation parameters may be measured in a manner known to those in the art, using the systems in FIGS. 1A and 2. Another aspect of the invention is based on the observation that certain radiation parameters may be more sensitive to the change in one or more parameters associated with the profile type and related films than other radiation parameters. This is illustrated in FIG. 6C. From the profile type, its associated film(s) and the initial values 252 of the parameters selected, the diffraction solver 108 generates predicted spectra of different radiation parameters. Shown as examples in FIG. 6C are the spectra 270 for four different radiation parameters that are so generated: $R_s$, $R_p$, cos Δ and tan ψ. The different parameter values (e.g. CD, H, SWA) associated with the profile type are then varied and the diffraction solver 108 is used to generate a set of different spectra for each of the four or more different radiation parameters. By comparing the change in spectra of the four or more radiation parameters corresponding to the same variation in parameter value (e.g. CD, H, SWA), the radiation parameter and its corresponding spectra that is the most sensitive to the change in parameter value is then identified.

In other words, each of the selected profile types is varied. Thus, if the profile type of FIG. 4A is selected, then each of the parameters CD, H and SWA is varied. For each variation of each of the three parameters, diffraction solver 108 computes the corresponding spectrum for each of the four or more radiation parameters. A quantity $\chi^2$ may be defined by the equation:

$$\chi^2 = \frac{1}{N} \sum_{n=1}^{N} \frac{[R_1(\lambda_n) - R_2(\lambda_n)]^2}{\sigma_n^2}$$

This quantity ($\chi^2$) measures the difference between two sets of data $R_1$ and $R_2$, which can be, e.g., the theoretical and the experimental values of a certain signal ($R_s$, $R_p$, cos $\Delta$, . . . ). The values $\sigma_n$ set the weight of the n-th data point and are typically defined by the experimental uncertainty. In calculating $\chi^2$ in FIG. 6C, actually two theoretical spectra are compared—one at the initial parameter values with the one at a modified parameter values. Quantities other than $\chi^2$ may also be used in optimization for example, the cross-correlation between the compared spectra may be optimized.

The quantity $\chi^2$, along path 254, is thus computed according to the equation above, which is the difference between two theoretical spectra—one at the initial parameter values 252 and the one where one of the parameter values has been modified from its initial value. In the four sets of spectra 270 shown in FIG. 6C, a number of curves are computed for each of the four radiation parameters, where each curve corresponds to the theoretical spectrum with one of the parameters having a value that is modified compared to the initial value. The four quantities $\chi^2$ of the four radiation parameters corresponding to the same modification in CD, H or SWA are then compared to identify the radiation parameter that is the most sensitive to a change in CD, H or SWA, and its spectra. In the example 274 shown in FIG. 6C, $\chi^2$ is the largest for the radiation parameter tan ψ. Therefore, if the radiation parameter tan ψ is chosen for the modeling process shown in FIG. 5A, a more accurate result may be achievable. In other words, when the apparatus of FIG. 1A or 2 is used to measure the spectra associated with the diffracting structure and any associated films (block 120 in FIG. 5A), the radiation parameter tan ψ is measured over a range of wavelengths, and such spectrum is then compared (block 122) to tan ψ generated by the diffraction solver 108 in the flowchart of FIG. 5A, to arrive at a more accurate set of values for the final set 260 of FIG. 6B.

FIG. 6C illustrates four of the radiation parameters that may be used. A more complete list includes the following 12 radiation parameters:

$$R_s, R_p, R_s - R_p, \cos\Delta, \tan\psi = |r_p/r_s|,$$

$$R_s/R_p, X = |r_s - r_p|^2, Y = |r_s + r_p|^2, X/Y, (X-Y)/(X+Y)$$

$$\alpha = \frac{R_p \cos^2 A - R_s \sin^2 A}{R_p \cos^2 A + R_s \sin^2 A},$$

$$\beta = \frac{2\sqrt{R_p \cos^2 A} \sqrt{R_s \sin^2 A}}{R_p \cos^2 A + R_s \sin^2 A} \cos\Delta$$

where $r_s$ and $r_p$ denote the complex amplitude reflection coefficients for S and P polarizations respectively, while $R_s$ and $R_p$ are the reflectivities for S and P polarizations respectively: $R_s = |r_s|^2$, $R_p = |r_p|^2$. The angle A is the analyzer angle and can be (optimally) set by hardware configuration. The quantities tan ψ and cos Δ are ellipsometric parameters known to those in the art.

It will be noted that the process described in reference to FIGS. 5A, 5B takes into account both profile and film parameters, so that the process described above in reference to FIG. 6C selects the radiation parameter and its associated spectra that is the most sensitive to a variation in a profile and/or film parameter.

The advantages provided by different aspects of the process described above are set forth in the table below.

| FIGS. 6A, 6B, 6C. Off-line techniques developed and used in this invention that allow real-time measurement of profile and film stack parameters by the method of FIGS. 5A, 5B | |
|---|---|
| Method | Advantage |
| Analysis of manufacturing process information by a lithography simulation tool (FIG. 6A). | Optimal choice of profile model and process window for parameters |
| Selection of one or more signals (spectra) that are most sensitive to parameters of interest (FIG. 6C) | Ability to measure both profile and film parameters by selecting most sensitive signals |
| Generation of a look-up table of eigenvalues in the grating region | Replacement of the eigenvalue computation by interpolation to speed up the diffraction solver in the real-time measurement |
| Generation of a coarse library of spectra within the process window (FIG. 6B) | Best initial seed to accelerate the convergence of nonlinear optimization |

FIG. 7 is a block diagram of an integrated spectroscopic diffraction-based metrology system, a photolithographic track/stepper and an etcher to illustrate another aspect of the invention. A layer of material such as photoresist is formed on the surface of a semiconductor wafer by means of track/stepper 350, where the photoresist forms a grating structure on the wafer. One or more of the CD, H, SWA and/or other parameters of the grating structure are then measured using systems 10, 80 of FIG. 1A, 2 and one or more of the above-described techniques may be employed if desired to find the value(s) of the one or more parameters of the photoresist pattern and its associated film(s). Such value(s) from the computer 40 are then fed back to the track/stepper 350, where such information may be used to alter the lithographic process in track/stepper 350 to correct any errors. In semiconductor processing, after a layer of photoresist has been formed on the wafer, an etching process may be performed, such as by means of etcher 360. The layer of photoresist is then removed in a manner known in the art and the resulting grating structure made of semiconductor material on the wafer may again be measured if desired using system 10 or 80. The value(s) measured using any one or more of the above-described techniques may be supplied to the etcher for altering any one of the etching parameters in order to correct any errors that have been found using system 10 or 80. Of course, the results obtained by one or more of the above described techniques in system 10, 80 may be used in both the track/stepper and the etcher, or in either the track/stepper or the etcher but not both. The track/stepper 350 and/or etcher 360 may form an integrated single tool with the system 10 or 80 for finding the one or more parameters of a diffracting structure, or may be separate instruments from it.

FIG. 8 is a schematic view of the track/stepper 350 and an associated flowchart illustrating a process for semiconductor wafer processing to illustrate in more detail the points of integration of the processing process with the detection of profiles of diffracting structures and associated films to illustrate in more detail a part of the process in FIG. 7. As shown in FIG. 8, a semiconductor wafer 352 may be loaded from a cassette loader 354 to several stations labeled "prime," "coat," "soft bake," "EBR." Then the wafer 352 is delivered by a stepper interface 356 to exposure tool 358. The different processes at the four locations mentioned above are set forth below:

At the location "Prime", the wafer undergoes chemical treatment before a layer of photoresist is spun on it, so that the photoresist layer can stick to wafer. At the location "Coat", a layer of photoresist coating is spun onto the wafer. At "Soft bake", the layer of resist is baked to remove chemical solvent from the resist. At "EBR" which stands for "edge-bead removal", a solvent nozzle or laser is used to remove excess photoresist from the edge of wafer.

After the wafer has been exposed to radiation by tool 358, the wafer then undergoes four additional processes: "PEB," "PEB chill," "Develop," and "Hard bake." At "PEB or post exposure bake", the wafer is baked to reduce standing-wave effect from the exposure tool. Then it is cooled at "PEB chill". The wafer is then washed with reagent to develop the photoresist, so that un-exposed (negative) or exposed (positive) photoresist is removed. The wafer then is baked at "Hard bake" to stabilize the photoresist pattern. It will be noted that all of the components of device 350 of FIG. 8 except for the "exposure tool" 358 is known as the "Track" (also called cluster).

After these latter four processes have been completed, the wafer 352 is then returned to the cassette loader 354 and this completes the processing involving the stepper 350. The detection system 10 or 80 may be applied at arrow 362 to measure the parameters of the diffracting structure and associated film(s). Thus, such parameters may be measured after "hard bake."

There are several ways of enabling a measurement of a profile using information coming from a separate film or another profile measurement:

a. Performing a film measurement to determine the thickness of underlying layers and feeding the information forward to a separate scatterometry measurement on a grating target of photo resist using regression. This reduces the number of variables in the regression, which speeds up significantly the calculation and improves the accuracy/robustness.

b. Performing a film measurement to determine the n&k of underlying layers (e.g. the BARC layer in a gate ADI measurement) and feeding the information forward to a separate scatterometry measurement on a grating target of photo resist using regression. This reduces the number of variables in the regression, which speeds up significantly the calculation and eliminates errors due to incorrect optical constants in a library or regression schemes.

c. Performing a film measurement to determine the thickness of underlying AND CURRENT etched layers (layers that are part of the grating structures) and feeding the information forward to a separate scatterometry measurement on a grating target of etched dielectric. This enables the measurements of damascene structures that otherwise would have too many degrees of freedom in the profile library or regression measurement.

d. Performing a profile measurement using a scatterometry and feeding it forward as the seed to the next scatterometry regression measurement e. Performing a scatterometry measurements and feeding the information (most significantly—side wall angle and pitch) to a CD-SEM measurement on the same target or a different target on the same wafer. This eliminates the uncertainty that exist in SEM algorithms with respect to the wall angle dependence of CD measurements. In addition, it gives the CD SEM an absolute calibration of the pitch.

f. Performing a scatterometry measurements and feeding the information (most significantly—Top rounding and wall angle) to an overlay measurement on the same target or a different target on the same wafer (e.g. the zebra targets). This eliminates the uncertainty that exist in overlay algorithms with respect to wafer-induced shifts (as a results of wafer processing variations).

g. Combine a multiple angle of illumination information either in a feed forward scheme or in a simultaneous regression to determine the profile parameters of a structure. For example the use of a normal or near normal reflectometer together with an oblique one to provide additional information on the structure (one or both can be an SE).

h. Performing a profile measurement using scattrometry by regression on the reflected signal or the phase signals as collected by the metrology tool (typically a spectroscopic ellipsometer)

i. Performing a regression to find the profile of a structure using a sub set of the collected spectra, polarization or phase information that is less sensitive to underlying film properties.

FIGS. 9A, 9B, 9C are schematic views of sample structures useful for illustrating different embodiments of the invention for determining the profile or parameters of a diffracting structure.

Thus, the film stack 360 as shown in FIG. 9A is measured at site 1 by means of a reflectometer, spectrophotometer or ellipsometer as illustrated in FIGS. 1A and 2 to obtain the thicknesses and/or complex indices of refraction of the different layers in the film stack. The instruments in FIGS. 1A and 2 may also be used to measure intensity and phase information from the diffracting structure 362a on top of the film stack 360 at site 2. If the film thickness and indices of refraction information obtained by measuring the film stack 360 at site 1 is used in the calculations or modeling of the radiation data in measuring structure 362 at site 2, the number of variables in the regression or calculation will be drastically reduced. This significantly speeds up the calculation of the profile and/or parameters (e.g. critical dimension, side wall angle and thickness) of the diffracting structure 362a.

In some applications, the film stack that is available for measurement at site 1 may not be identical to the film stack associated with the diffracting structure; this is illustrated in FIG. 9B. Thus, the film stack 364 measured at site 1 is different from the film stack 366 over or below a diffracting structure 368a of the overall structure 368. However, as long as there is one common layer between the film stacks 364, 366, measurement of the stack 364 may still yield information useful for simplifying the measurement of the diffracting structure 368a. Thus, as shown in FIG. 9B, the two film stacks 364, 366 have a substantially identical layer 370. In such event, knowledge of the thickness and the complex index or refraction of layer 370 would simplify the calculation or regression process in determining the profile or parameters of the diffracting structure 368a. This is true even where the two layers 370 in the two stacks 364, 366 are not identical, but have substantially the same thickness or the same index of refraction or other optical properties.

FIGS. 9A, 9B illustrate structures obtained more frequently in lithographic processing. During etching processes, frequently only one portion of a layer may be etched while leaving another portion of the layer unetched. In such event, measurement of the unetched portion may help to simplify the determination of the profile or parameters of the diffracting structures in the etched portion. This is illustrated in FIG. 9C. As shown in FIG. 9C, the unetched portion 372 includes layers 0, 1 and 2. Prior to etching, layers 0, 1, 2 of portion 374 are substantially the same as those in portion 372. During etching, layer 2 has been etched into diffracting structure 374a of the overall structure 374. Therefore, if structure 372 at site 1 is measured by means of the apparatus in FIG. 1A or 2, the information concerning the thicknesses and the indices of refraction of the three layers in structure 372 would greatly reduce the complexity of the calculation or optimization process for deriving the profile or parameters of the diffracting structure 374a.

The above-described feature is applicable even where layers 0 and 1 and the corresponding layers in structure 374 are not identical, or when layer 2 of structure 372 does not have the same thickness or index or refraction as the diffracting structure 374a. As long as there is some common parameter such as thickness or index or refraction between any one layer in structure 372 and another layer in the structure 374, measuring structure 372 at site 1 and feeding the information forward to the measurement of structure 374 would simplify the second measurement.

FIG. 10 illustrates an embodiment where data obtained from a scatterometric measurement tool 376 may be fed forward to a CD-SEM measurement tool 378 performing a measurement on the same target or a target with some common features (in the same sense as those discussed above in reference to FIG. 9C).

FIG. 10 also illustrates an embodiment where data obtained from a scatterometric measurement tool 376 may be fed forward to an overlay measurement tool 378 performing a measurement on the same target on a target with some common features (in the same sense as those discussed above in reference to FIG. 9C).

FIG. 11 is a schematic view of an overlay tool measuring the offset between two gratings (only one grating 382 is shown in FIG. 11). A radiation beam 381 is reflected by mirrors 385 and focused by lens 384 to the target 382. The scattered or diffracted radiation is collected by lens 386 and focused to CCD 387, whose output is sent to computer 40 to compute the misalignment between the gratings. Alternatively, the target may be a box-in-box type target, a one-dimensional image of which is shown in FIG. 12. The profiles of both types of the target will influence the overlay measurements. Thus, as illustrated in FIG. 12, the shape of the edges of a box-in-box type target can have an effect on the radiation diffracted by the box-in-box target. Therefore, by measuring the profile or other parameters of the target, and feeding this information to the overlay measurement tool, the overlay measurement will be more accurate.

In FIG. 6C, and the accompanying description above, it is noted that it may be possible to select an optimum parameter for the matching process in order to obtain a more accurate result for the parameter values. In some applications, the reverse may be desirable. Thus, where it is desirable to measure the profile or parameters of a diffracting structure that is adjacent to a film structure, but where the thicknesses and indices of refraction of the film structure are not readily available or cannot be measured, it may be desirable to choose parameters where the influence of the film structures on the diffracting structure measurement is minimized. For such applications, essentially the same process as that described above in reference to FIG. 6C may be carried out. In contrast to the discussion of FIG. 6C, however, instead of selecting the parameter (e.g. film thickness or indices of refraction) of the film structure by which the spectral variations are maximized for a given change in the parameter value, the film parameter which gives rise to the smallest change in the spectral variations when it is changed is selected instead.

Software Upgrades

The invention has been described above, employing a system such as that shown in FIGS. 1A, 2 and 11. While the various optical components in the system of FIGS. 1A 2 and 11 are used to obtain measured data from the sample, many of the other processes are performed by computer 40 (not shown in FIG. 2 to simplify the figure). Thus, for many systems currently being used by manufacturers such as semiconductor manufacturers, the computers used in the systems may not have the capability to perform the techniques described above. Thus, another aspect of the invention envisions that the software in these computers can be upgraded so that computer 40 can perform one or more of the above described different functions. Therefore, another aspect of the invention involves the software components that are loaded to computer 40 to perform the above-described functions. These functions, in conjunction with the optical components of system 10 or 80 or 380 in FIG. 1A or 2 or 11, provide results with the different advantages outlined above. The software or program components may be installed in computer 40 in a variety of ways.

As will be understood in the art, the inventive software components may be embodied in a fixed media program component containing logic instructions and/or data that when loaded into an appropriately configured computing device to cause that device to perform according to the invention. As will be understood in the art, a fixed media program may be delivered to a user on a fixed media for loading in a users computer or a fixed media program can reside on a remote server that a user accesses through a communication medium in order to download a program component. Thus another aspect of the invention involves transmitting, or causing to be transmitted, the program component to a user where the component, when downloaded into the user's device, can perform any one or more of the functions described above.

FIG. 13 shows an information appliance (or digital device) that may be understood as a logical apparatus that can read instructions from media 417 and/or network port 419. Apparatus 40 can thereafter use those instructions to direct server or client logic, as understood in the art, to embody aspects of the invention. One type of logical apparatus that may embody the invention is a computer system as illustrated in 40, containing CPU 404, optional input devices 409 and 411, disk drives 415 and optional monitor 405. Fixed media 417 may be used to program such a system and may represent a disk-type optical or magnetic media, magnetic tape, solid state memory, etc. One or more aspects of the invention may be embodied in whole or in part as software recorded on this fixed media.

Communication port 419 may also be used to initially receive instructions that are used to program such a system to perform any one or more of the above-described functions and may represent any type of communication connection, such as to the internet or any other computer network. The instructions or program may be transmitted directly to a user's device or be placed on a network, such as a website of the internet to be accessible through a user's device. All such methods of making the program or software component available to users are known to those in the art and will not be described here.

The invention also may be embodied in whole or in part within the circuitry of an application specific integrated circuit (ASIC) or a programmable logic device (PLD). In such a case, the invention may be embodied in a computer understandable descriptor language which may be used to create an ASIC or PLD that operates as herein described.

While the invention has been described above by reference to various embodiments, it will be understood that changes and modifications may be made without departing from the scope of the invention, which is to be defined only by the appended claims and their equivalents. All references referred to herein are incorporated by reference in their entireties.

What is claimed is:

1. A method for measuring one or more parameters associated with a diffracting structure, said diffracting structure located adjacent to one or more first film structures, said diffracting structure or at least a first layer of said one or more first film structures comprising a first material and having associated thickness and optical index information, comprising:

measuring data associated with a second structure, said second structure and said diffracting structure or said at least first layer formed from the same manufacturing process, said second structure having substantially the same thickness as the diffracting structure or said at least first layer, and/or comprises a second material having substantially the same optical properties as those of the first material;

directing a beam of electromagnetic radiation at a plurality of wavelengths at said diffracting structure and the one or more first film structures;

detecting intensity and/or phase data of a diffraction at said plurality of wavelengths from said diffracting structure of said beam; and determining said one or more parameters using the data associated with the second structure and data detected from said diffracting structure in an optimization process, wherein the determining includes feeding forward the data associated with the second structure to said optimization process to simplify the optimization process for determining said one or more parameters.

2. The method of claim 1, wherein said second structure is located adjacent to a film structure comprising layers, at least one of which has substantially the same thickness as one layer in the one or more first film structures, comprises a material having substantially the same optical properties and is formed from the same manufacturing process as those of a material in the one or more first film structures, said method further constructing a reference database of the one or more parameters using thickness and optical index information of the film structure adjacent to the second structure, wherein said determining uses the reference database.

3. The method of claim 2, wherein said constructing constructs a reference database comprising a plurality of functions, each of said functions corresponding to a probable linewidth, height or wall angle of said diffracting structure.

4. The method of claim 2, wherein said constructing constructs a reference database over a spectrum of wavelengths, said directing directs a beam of broadband radiation at wavelengths including said spectrum and said detecting detects intensity or ellipsometric parameter data over said spectrum of wavelengths.

5. The method of claim 1, said parameters including critical dimension, height and sidewall angle.

6. The method of claim 1, wherein said one or more first film structures have no periodic diffracting pattern thereon, and the measuring measures by means of a spectroscopic ellipsometer, a spectrophotometer or a spectroreflectometer.

7. The method of claim 1, wherein said directing and detecting are by means of a spectroscopic ellipsometer, a spectrophotometer or a spectroreflectometer.

8. The method of claim 1, further comprising providing information concerning optical index or indices and film thickness(es) of the one or more first film structures, and constructing a reference database of the one or more parameters related to the diffracting structure using said optical index and film thickness information of the one or more first film structures, wherein said determining uses the reference database.

9. The method of claim 8, wherein said constructing constructs a reference database comprising a plurality of functions, each of said functions corresponding to a probable linewidth, height or wall angle of said diffracting structure.

10. The method of claim 8, wherein said constructing constructs a reference database over a spectrum of wavelengths, and said directing directs a beam of broadband radiation at wavelengths including said spectrum and said detecting detects intensity or ellipsometric parameter data over said spectrum of wavelengths.

11. The method of claim 1, wherein said directing directs polarized radiation to the diffracting portion.

12. The method of claim 1, said plurality of wavelengths including ultraviolet wavelengths.

13. A method for measuring one or more parameters of a first periodic diffracting structure of a sample, comprising:

performing measurements on a second structure to obtain intensity or phase data, and yielding a profile of such structure;

performing scatterometric measurements on the first diffracting structure to obtain intensity or phase data; and obtaining the one or more parameters of the first diffracting structure using results from the measurements on the second structure, said obtaining including an optimization process employing the profile of the second structure as a seed profile that is fed forward to the optimization process, wherein said optimization process includes a regression process that uses said seed profile as a seed for the regression process.

14. The method of claim 13, wherein both diffracting structures are of the same sample, so that both scatterometric measurements are performed on the sample.

15. The method of claim 13, wherein layers in the first and second structures are the same, wherein each layer in the first structure is the same as and corresponds to a layer in the second structure, except that at least one layer in the first structure is periodic and at least one layer in the second structure corresponding to said at least one periodic layer in the first structure is not.

16. The method of claim 15, wherein said at least one layer in the first structure is the same as said at least one corresponding layer in the second structure prior to an etching process of the said at least one layer in the first structure.

17. The method of claim 13, wherein both structures are of different samples.

18. A method for measuring one or more parameters of a sample having one or more periodic diffracting structures thereon, comprising:
   performing scatterometric measurements on a first one of the diffracting structures to obtain intensity or ellipsometric data;
   performing SEM measurements on a second one of the diffracting structures to obtain critical dimension or profile data, the second one being the same or different from the first diffracting structure; and
   obtaining the one or more parameters on the second diffracting structure using results from the measurements on the first diffracting structure.

19. The method of claim 18, wherein said obtaining obtains an absolute calibration of pitch of the second diffracting structure.

20. A method for measuring one or more parameters of a sample having a plurality of periodic diffracting structures thereon, comprising:
   performing scatterometric measurements on a first one of the diffracting structures to obtain intensity or ellipsometric data;
   performing overlay measurements on a pair of the diffracting structures or lines or bars or boxes useful for deriving misalignment information between the pair; and
   deriving the misalignment information between the pair from result of the overlay measurements wherein a result of scatterometric measurements is employed to derive the misalignment information.

21. The method of claim 20, wherein the result of scatterometric measurements comprises critical dimension, height, sidewall angle or profile of the first diffracting structure.

22. A method for measuring one or more parameters of a periodic diffracting structure with an adjacent film structure having associated thickness and optical index information, comprising:
   providing a profile type for the periodic diffracting structure and the film structure, said profile type associated with one or more parameters related to the periodic diffracting structure and information related to the film structure, said profile type also associated with a plurality of sets of radiation data of different radiation parameters, said radiation parameters including reflectance or transmittance parameters and ellipsometric parameters;
   selecting at least one set of radiation data from the sets of radiation data of different parameters associated with the profile type based on sensitivity of such data to a change in the information associated with the film structure as derived from the film structure or the periodic diffracting structure;
   detecting radiation data from the periodic diffracting structure; and
   comparing the detected radiation data to the set selected to arrive at a set of value(s) of the one or more parameters.

23. The method of claim 22, wherein said providing comprises:
   supplying a gallery of a plurality of profile types, each profile type associated with one or more parameters related to the periodic diffracting structure and information associated with the film structure and associated with a set of radiation data, wherein at least one of said profile types provided is associated with a plurality of sets of radiation data of different radiation parameters, said radiation parameters including reflectance or transmittance parameters and ellipsometric parameters; and
   selecting a profile type from the gallery.

24. The method of claim 22, wherein said selecting selects the at least one set of radiation data based on a criterion that the selected at least one set is less sensitive than the non selected sets to a change in the information associated with the film structure.

* * * * *